(12) United States Patent
Gushurst et al.

(10) Patent No.: US 8,563,571 B2
(45) Date of Patent: Oct. 22, 2013

(54) CRYSTALLINE FORMS OF OXYMORPHONE HYDROCHLORIDE

(75) Inventors: Karen S. Gushurst, West Lafayette, IN (US); Leonard J. Chyall, Lafayette, IN (US); Lien H. Koztecki, Indianapolis, IN (US); Brenton Skylar Wolfe, West Lafayette, IN (US)

(73) Assignee: Noramco, Inc., Athens, GA (US)

( * ) Notice: Subject to any disclaimer, the term of this patent is extended or adjusted under 35 U.S.C. 154(b) by 263 days.

(21) Appl. No.: 13/187,854

(22) Filed: Jul. 21, 2011

(65) Prior Publication Data

US 2012/0022093 A1  Jan. 26, 2012

Related U.S. Application Data

(60) Provisional application No. 61/366,690, filed on Jul. 22, 2010.

(51) Int. Cl.
*A61K 31/485* (2006.01)
*C07D 489/04* (2006.01)

(52) U.S. Cl.
USPC .............................................. 514/282; 546/45

(58) Field of Classification Search
USPC ............................................ 514/282; 546/45
See application file for complete search history.

(56) References Cited

U.S. PATENT DOCUMENTS

| | | |
|---|---|---|
| 7,851,482 B2 | 12/2010 | Dung et al. |
| 8,134,002 B2 | 3/2012 | Huang |
| 8,217,175 B2 | 7/2012 | Wang et al. |
| 8,357,802 B2 | 1/2013 | Huang |

FOREIGN PATENT DOCUMENTS

WO    WO 2012/163796 A1 * 12/2012

* cited by examiner

*Primary Examiner* — Charanjit Aulakh

(57) ABSTRACT

The present invention is directed to crystalline forms of oxymorphone hydrochloride.

22 Claims, 24 Drawing Sheets

DSC (solid line) and TGA (broken line) profiles for oxymorphone HCl, crystalline Form A Automated sorption (open circle) /desoption (filled circle) profile measured for oxymorphone HCl, crystalline Form A

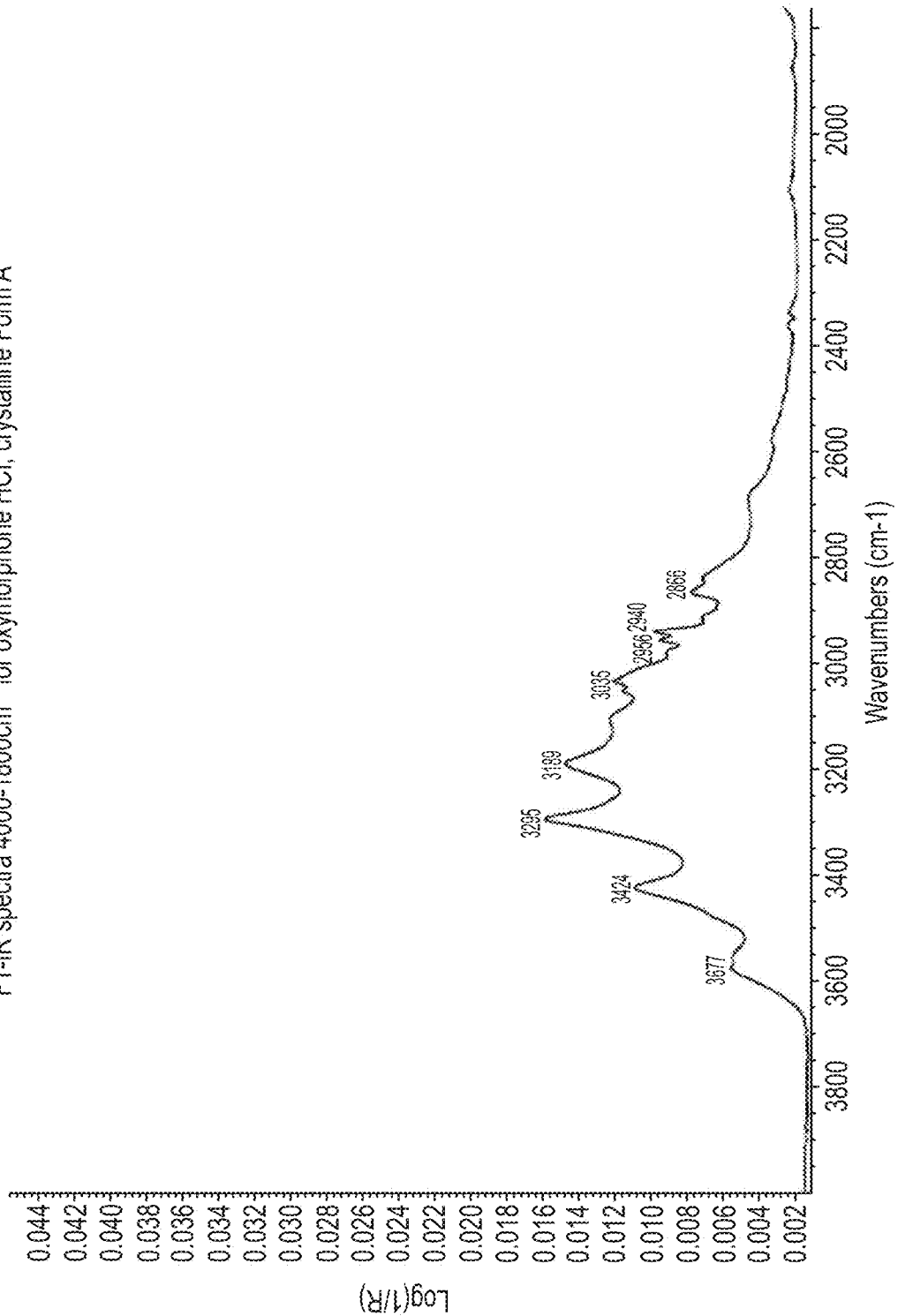

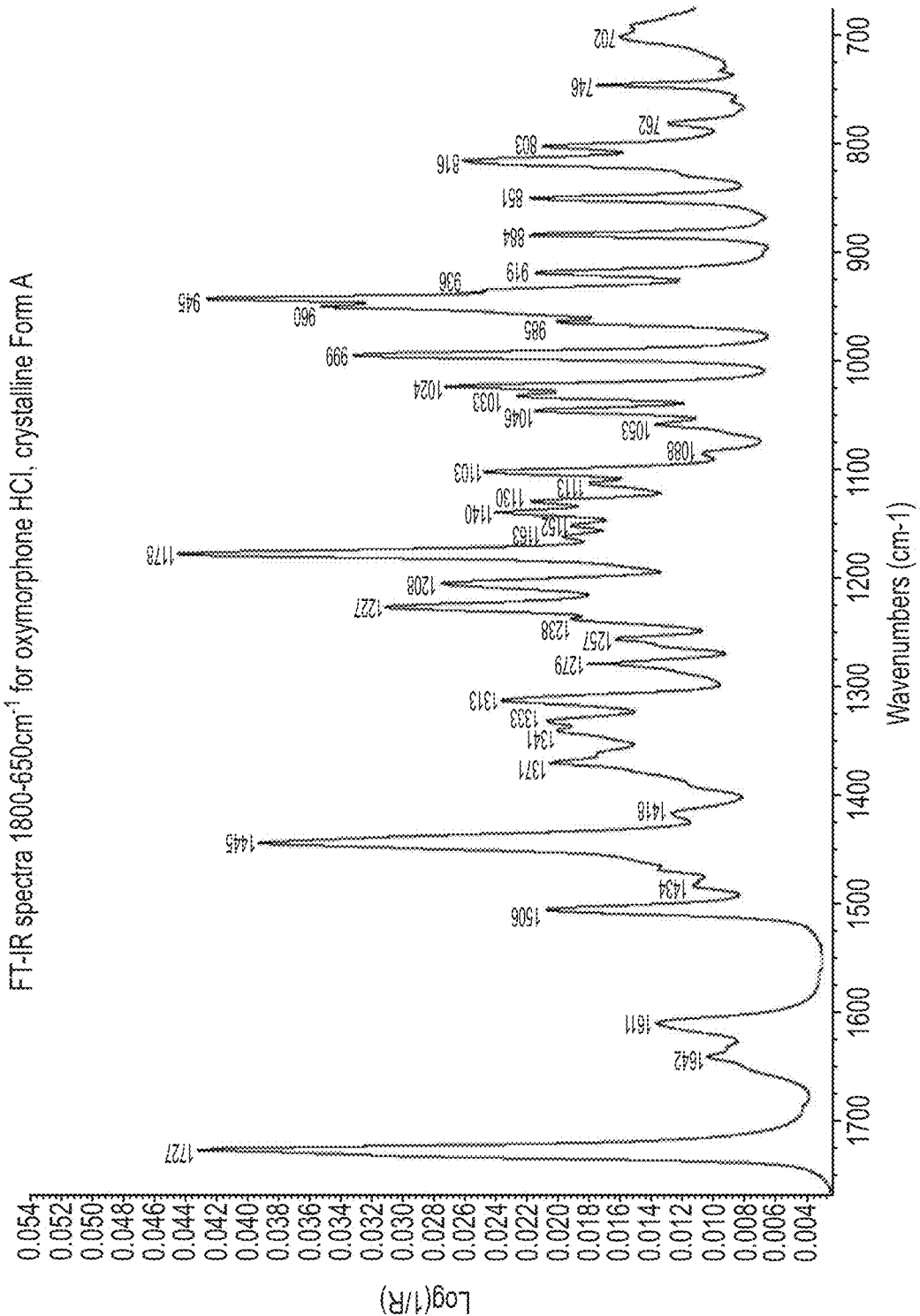
FIG. 14B FT-IR spectra 1800-650cm⁻¹ for oxymorphone HCl, crystalline Form A FT-IR spectra 4000-1800cm⁻¹ for oxymorphone HCl, crystalline Form B

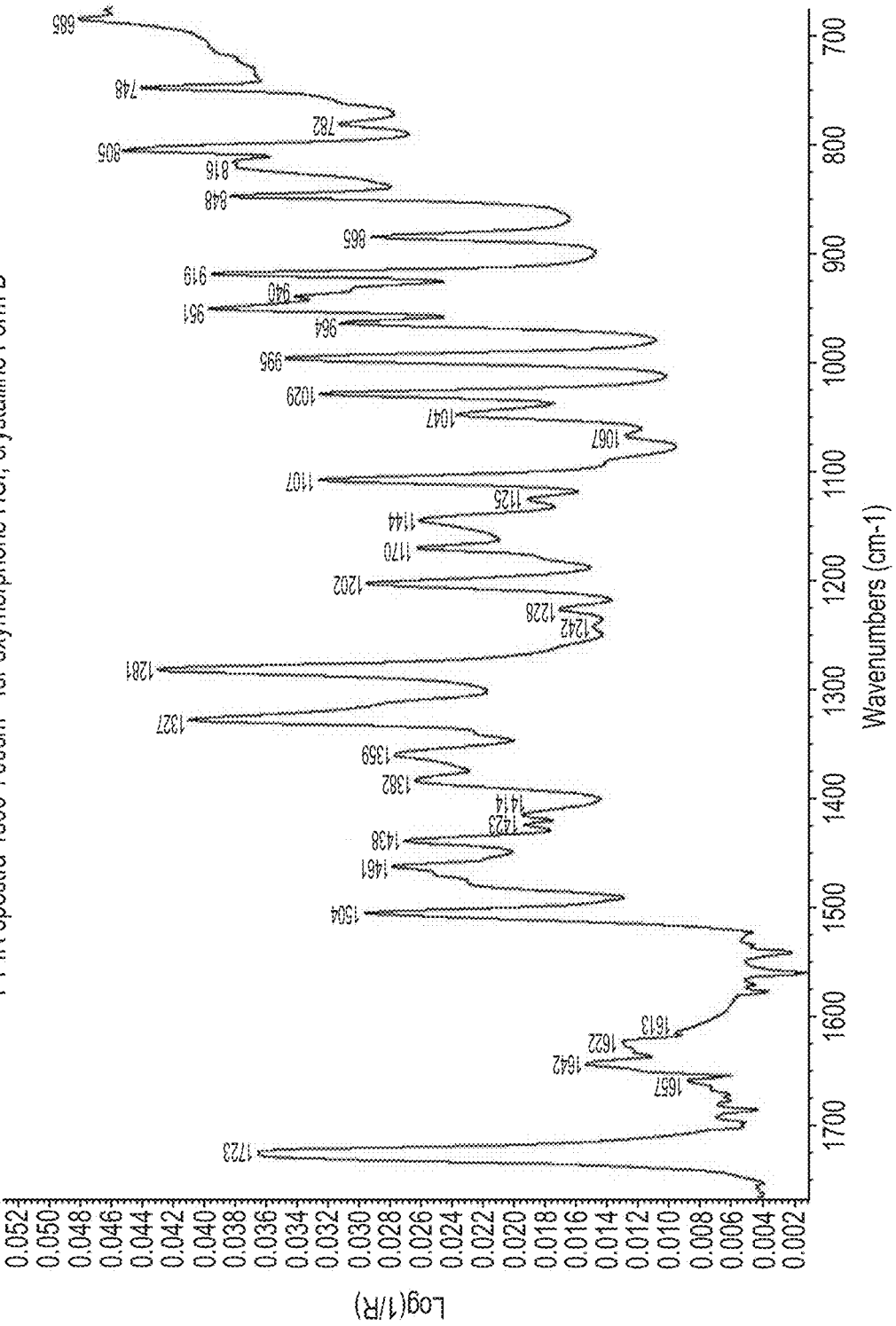

TGA profile for oxymorphone HCl, crystalline Form C

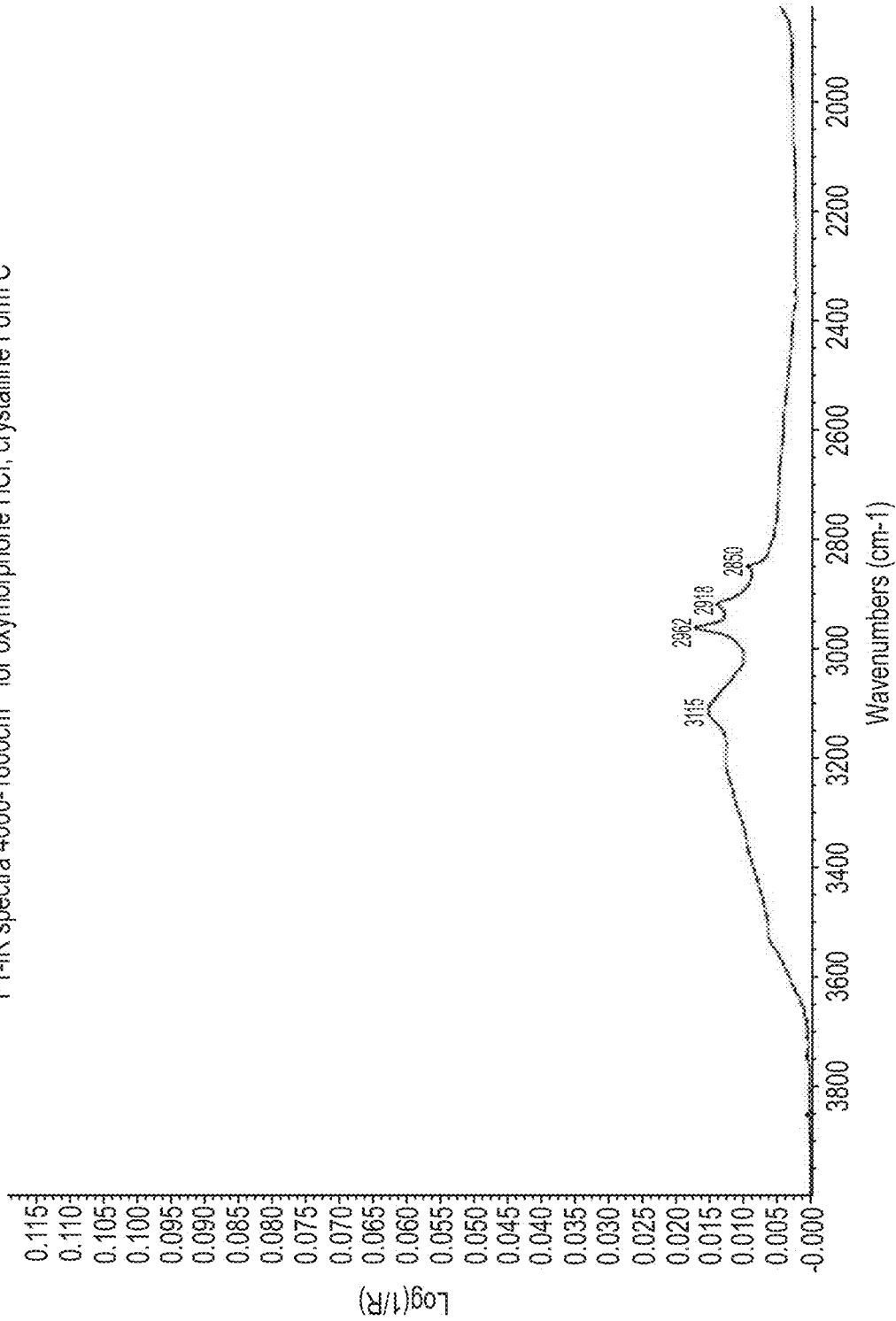

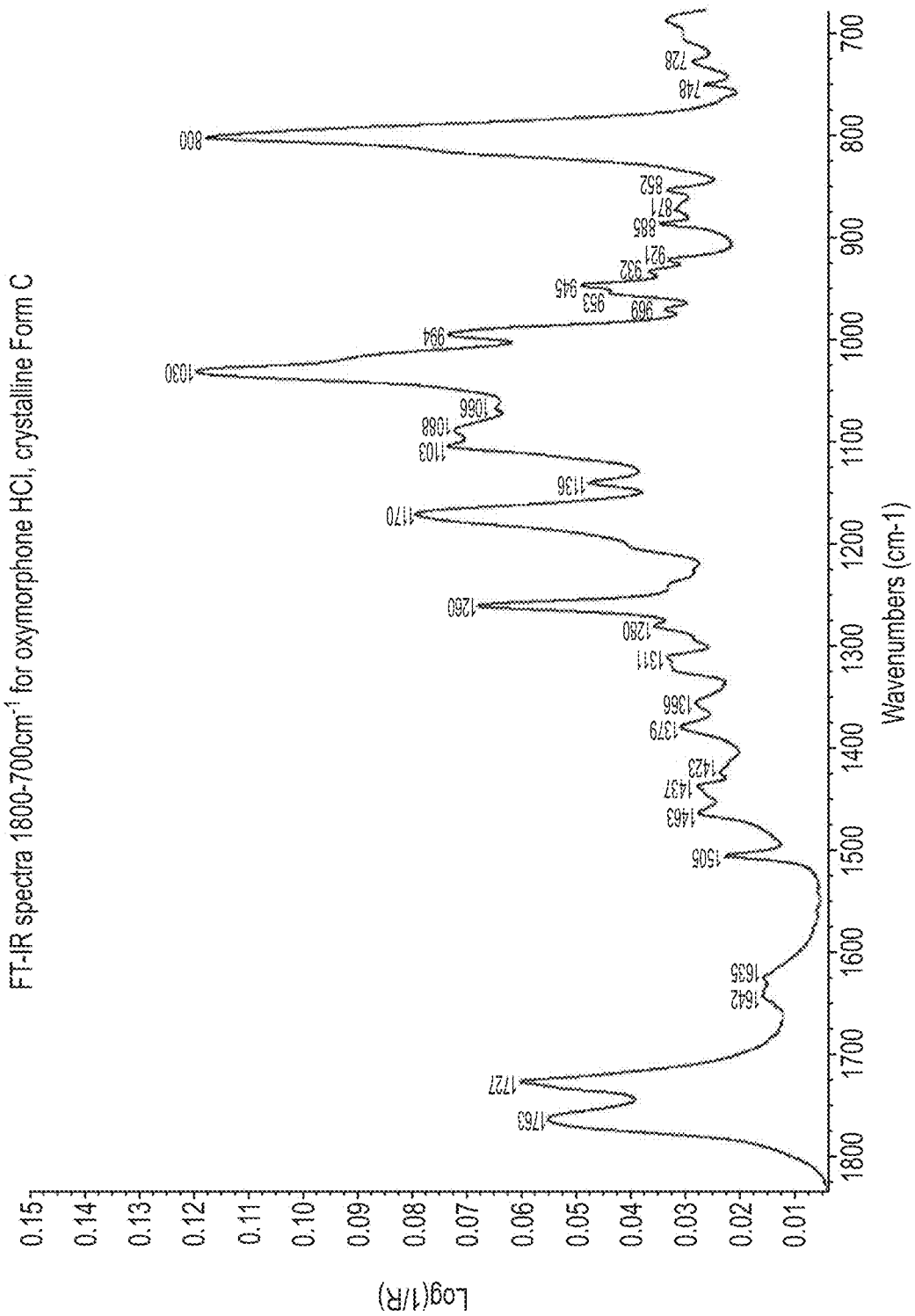

DSC profile for oxymorphone HCl, crystalline Form M

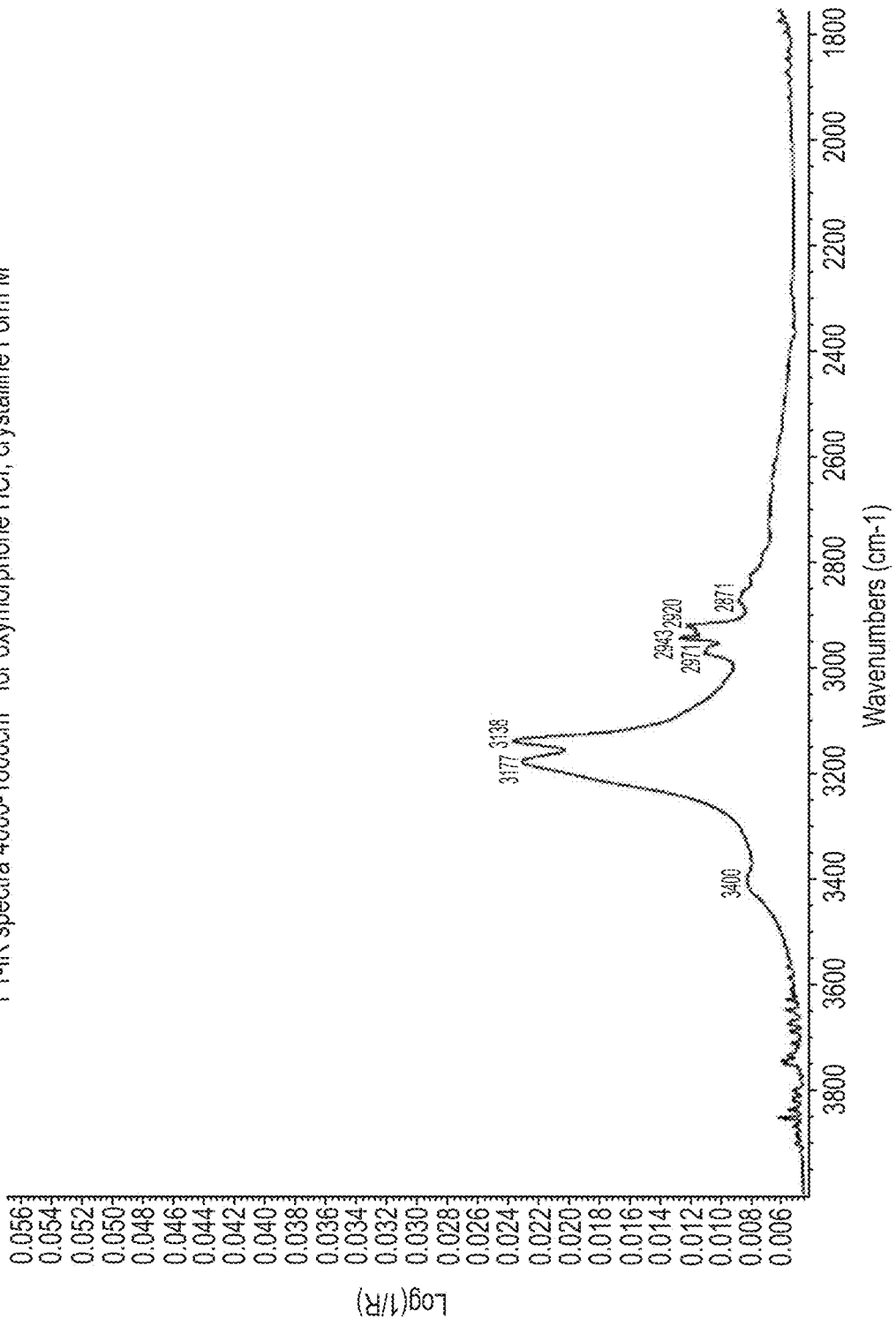

FT-IR spectra 1800-700cm⁻¹ for oxymorphone HCl, crystalline Form M

CRYSTALLINE FORMS OF OXYMORPHONE HYDROCHLORIDE

CROSS-REFERENCE TO RELATED APPLICATIONS

This application claims priority from U.S. Provisional Application Ser. No. 61/366,690 filed Jul. 22, 2010, the contents of each of which are hereby incorporated by reference in their entirety.

FIELD OF THE INVENTION

The present invention is directed to crystalline forms of oxymorphone hydrochloride.

BACKGROUND OF THE INVENTION

Oxymorphone hydrochloride, also known as 4,5-epoxy-3,14-dihydroxy-17-methyl-(5α)-morphinan-6-one hydrochloride (1:1), or 1,4-hydroxydihydromorphinone, ($C_{17}H_{20}ClNO_4$, MW 337.80) is a semi-synthetic opioid analgesic. The chemical structure of oxymorphone hydrochloride is shown below

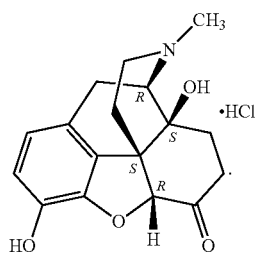

Oxymorphone HCl is indicated for the relief of moderate to severe pain. Oxymorphone HCl is also indicated as a pre-operative medication to alleviate apprehension, maintain anesthesia and as an obstetric analgesic. Additionally, oxymorphone HCl may be used to alleviate pain in patients with dyspnea associated with acute left ventricular failure and pulmonary edema.

SUMMARY OF THE INVENTION

The present invention is directed to ten novel crystalline forms of oxymorphone HCl. These forms are identified herein as Forms B, C, D, F, G, H, J, K, L and M. The known form of oxymorphone HCl is referred to hereinafter as oxymorphone HCl Form A.

The present invention is further directed to processes for the preparation of the novel crystalline forms of oxymorphone HCl as herein defined.

Illustrative of the invention is a pharmaceutical composition comprising a pharmaceutically acceptable carrier and any of the novel crystalline forms of oxymorphone HCl as herein defined. An illustration of the invention is a pharmaceutical composition made by mixing any of the novel crystalline forms of oxymorphone HCl as herein defined and a pharmaceutically acceptable carrier. Illustrating the invention is a process for making a pharmaceutical composition comprising mixing any of the novel crystalline forms of oxymorphone HCl as herein defined and a pharmaceutically acceptable carrier.

Exemplifying the invention are methods of providing analgesia, comprising administering to a subject in need thereof, a therapeutically effective amount of one or more of the novel oxymorphone HCl crystalline forms or pharmaceutical compositions described above.

BRIEF DESCRIPTION OF THE DRAWINGS

FIG. 14, parts A and B, illustrate an FT-IR spectra for oxymorphone HCl crystalline Form A.

FIG. 19, parts A and B, illustrate an FT-IR spectra for oxymorphone HCl crystalline Form C.

DETAILED DESCRIPTION OF THE INVENTION

Figure 1:
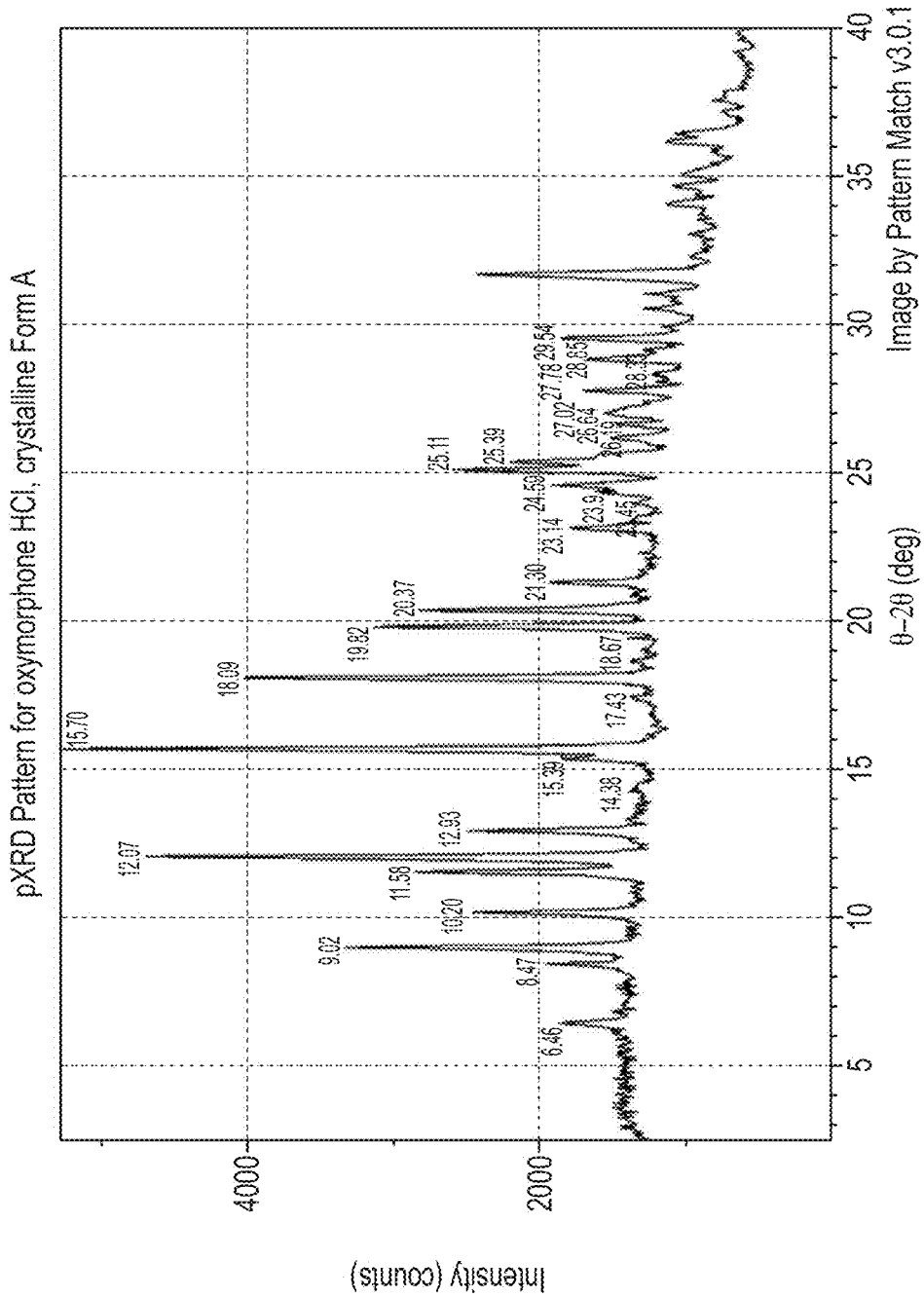
FIG. 1 illustrates a powder X-ray diffraction pattern of oxymorphone HCl crystalline Form A, expressed in terms of °2θ.

The present invention is directed to 10 novel forms of oxymorphone HCl, as herein described in detail. More particularly, the present invention is directed to novel crystalline forms B, C, D, F, G, H, J, K, L and M of oxymorphone HCl.

As used herein the term "oxymorphone hydrochloride" or "oxymorphone HCl" when used alone and without modifiers, refers to the known form or Form A of oxymorphone hydrochloride.

The present invention is further directed to processes for the preparation of the novel crystalline forms of oxymorphone HCl, as described in more detail in the Examples which follow herein. In an embodiment, the crystalline forms of oxymorphone HCl are prepared in an isolated form. In another embodiment, the crystalline forms of oxymorphone are prepared in a substantially pure form. In another embodiment, the crystalline form of oxymorphone is prepared in a form which is substantially free of other novel and/or crystalline forms of oxymorphone HCl.

As used herein, unless otherwise noted, the term "isolated form" shall mean that the compound is present in a form which is separate from any solid mixture with another compound(s), solvent system or biological environment. In an embodiment, the present invention is directed to crystalline forms of oxymorphone HCl as described herein, wherein said crystalline forms are present as an isolated form.

As used herein, unless otherwise noted, the term "substantially pure form" shall mean that the mole percent of impurities (including, but not limited to other crystalline forms of oxymorphone HCl, solvents, and/or other undesirable non-oxymorphone HCl impurities) in the isolated form is less than about 5 mole percent, preferably less than about 2 mole percent, more preferably, less than about 0.5 mole percent, most preferably, less than about 0.1 mole percent. In an embodiment, the present invention is directed to crystalline forms of oxymorphone HCl as described herein, wherein said crystalline forms are present as substantially pure form.

As used herein, unless otherwise noted, the term "substantially free of any other crystalline form(s)" when used to described a crystalline form of oxymorphone HCl shall mean that the mole percent of the other crystalline form(s) of oxymorphone HCl in the isolated or prepared form is less than about 10 mole percent, preferably less than about 5 mole percent, more preferably, less than about 1 mole percent, most preferably less than about 0.5 mole percent. In an embodiment, the present invention is directed to crystalline forms of oxymorphone HCl as described herein, wherein said crystalline forms are present as substantially free of any other crystalline form.

In an embodiment, the present invention is directed to a form of oxymorphone HCl as herein described, wherein the Form is between about 90% and about 100% pure, preferably between about 95% and about 100% pure, more preferably between about 98% and about 100% pure.

The present invention is further directed to the use of one or more of the novel crystalline forms of oxymorphone HCl instead of or in combination with the known Form A of oxymorphone HCl for its pharmacological effect. The present invention is further directed to pharmaceutical composition comprising a therapeutically effective amount of one or more of the novel crystalline forms of oxymorphone HCl, alone or in combination with the known Form A of oxymorphone HCl. The present invention is further directed to a method of providing a therapeutic (e.g., analgesic) effect to a mammal, preferably a human, in need thereof which comprises administering to said mammal a therapeutic amount of one or more of the novel crystalline forms of oxymorphone HCl, optionally in combination with the known Form A of oxymorphone HCl. Oxymorphone Form A, as herein defined, is known in the art, as are therapeutic uses and dose ranges, modes of administration, etc. for said Form A of oxymorphone HCl.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Crystalline Form Details

The novel crystalline forms of oxymorphone HCl of the present invention may be prepared directly or indirectly from oxymorphone free base and/or may be interconverted from other crystalline forms of oxymorphone HCl forms, more particularly from Form A or Form B. Examples 1-17 which follow herein, provide an example of the preparation of each of the crystalline forms of oxymorphone HCl.

The novel crystalline forms of oxymorphone HCl may be characterized by one or more of their characteristic physical properties, including, but not limited to their powder X-ray diffraction (pXRD) peaks, single crystal unit cell parameters, crystal structure, water content (as measured by Karl-Fischer), stability to cycling temperature and/or humidity, melting point and Fourier transform infrared spectra (FT-IR).

Powder X-Ray Diffraction Measurements

The crystalline forms of oxymorphone HCl were identified by their powder X-ray diffraction (pXRD) peaks/pattern. pXRD analyses on representative samples of the crystalline forms of oxymorphone HCl as herein described were performed using either an Inel XRG-300 diffractometer or a PANalytical X'Pert Pro diffractometer, as noted. Unless otherwise noted, the pXRD measurement conditions for each instrument were as follows.

INEL: Powder X-ray diffraction analyses were performed using an Inel XRG-3000 X-ray powder diffractometers with Cu Kα radiation. The Inel XRG-3000 diffractometer was equipped with a CPS (Curved Position Sensitive) detector with a 2θ range of 120°. Real time data were collected using Cu—Kα radiation starting at approximately 4°2θ at a resolution of 0.03°2θ. The tube voltage and amperage were set to 40 kV and 30 mA, respectively. The monochromator slit was set at 5 mm by 160 µm. The pattern was displayed from 2.5-40°2θ. Samples were prepared for analysis by packing them into thin-walled glass capillaries. Each capillary was mounted onto a goniometer head that was motorized to permit spinning of the capillary during data acquisition. The samples were analyzed for 5 min. Instrument calibration was performed using a silicon reference standard.

PANalytical: pXRD patterns were also collected using a PANalytical X'Pert Pro diffractometer. An incident beam of Cu Kα radiation was produced using an Optix long, fine-focus source. An elliptically graded multilayer mirror was used to focus the Cu Kα X-rays of the source through the specimen and onto the detector. Data were collected and analyzed using X'Pert Pro Data Collector software (v. 2.2b). Prior to the analysis, a silicon specimen (NIST SRM 640c) was analyzed to verify the Si 111 peak position. The specimen was sandwiched between 3 µm thick films, analyzed in transmission geometry, and rotated to optimize orientation statistics. A beam-stop and a helium atmosphere were used to minimize the background generated by air scattering. Soller slits were used for the incident and diffracted beams to minimize axial divergence. Diffraction patterns were collected using a scanning position-sensitive detector (X'Celerator) located 240 mm from the specimen.

One skilled in the art will recognize that the °2θ values and the relative intensity values were generated by performing a peak search on the measured data, whereas the d-spacing values were calculated from the °2θ values, using Cu Kα mean wavelength value of λ=1.5418 Å. One skilled in the art will further recognize that relative intensity for the measured peaks may vary significantly as a result of sample preparation, preferred orientation, etc. A variation of about ±20% is not atypical for these materials.

In an embodiment of the present invention, the crystalline form of oxymorphone HCl is characterized by pXRD peaks with a relative intensity of greater than about 10% and a °2θ angle of less than or equal to about 15.0°2θ. In another embodiment of the present invention, the crystalline form of oxymorphone HCl is characterized by pXRD peaks with a relative intensity of greater than about 25% and a °2θ angle of less than or equal to about 15.0°2θ. In another embodiment of the present invention, the crystalline form of oxymorphone HCl is characterized by pXRD peaks with a relative intensity of greater than about 25% and a °2θ angle of less than or equal to about 12.0°2θ.

Crystalline Form A

A representative sample of oxymorphone HCl crystalline Form A was analyzed using the INEL diffractometer as described above. Form A may be characterized by its pXRD peaks, as listed in Table A1, below. FIG. 1 illustrates a representative pXRD pattern for a representative sample of oxymorphone HCl crystalline form A.

TABLE A1 pXRD Observed peaks, Form A

| Position °2θ (±0.10) | d space (Å) | Relative Intensity (%) |
| --- | --- | --- |
| 6.46 | 13.679 ± 0.215 | 35 |
| 8.47 | 10.442 ± 0.125 | 37 |
| 9.02 | 9.803 ± 0.110 | 63 |
| 10.20 | 8.674 ± 0.086 | 46 |
| 11.58 | 7.641 ± 0.066 | 54 |
| 12.07 | 7.335 ± 0.061 | 89 |
| 12.93 | 6.847 ± 0.053 | 47 |
| 14.38 | 6.158 ± 0.043 | 25 |
| 15.39 | 5.759 ± 0.037 | 35 |
| 15.70 | 5.645 ± 0.036 | 100 |
| 17.43 | 5.088 ± 0.029 | 26 |
| 18.09 | 4.905 ± 0.027 | 76 |
| 18.67 | 4.752 ± 0.025 | 26 |
| 19.82 | 4.480 ± 0.022 | 59 |
| 20.37 | 4.360 ± 0.021 | 53 |
| 21.30 | 4.171 ± 0.019 | 36 |
| 23.14 | 3.844 ± 0.016 | 34 |
| 23.45 | 3.794 ± 0.016 | 26 |
| 23.97 | 3.713 ± 0.015 | 26 |
| 24.59 | 3.620 ± 0.015 | 36 |
| 25.11 | 3.546 ± 0.014 | 49 |
| 25.39 | 3.508 ± 0.014 | 42 |
| 26.19 | 3.403 ± 0.013 | 28 |
| 26.64 | 3.347 ± 0.012 | 28 |
| 27.02 | 3.300 ± 0.012 | 30 |
| 27.78 | 3.212 ± 0.011 | 32 |
| 28.33 | 3.150 ± 0.011 | 22 |
| 28.85 | 3.095 ± 0.011 | 31 |
| 29.54 | 3.024 ± 0.010 | 35 |

Oxymorphone HCl, crystalline Form A may be characterized by its powder XRD pattern which comprises peaks having a relative intensity of greater than or equal to about 35%, preferably peaks having a relative intensity of greater than or equal to about 50%.

Oxymorphone HCl, crystalline Form A may alternatively be characterized by its pXRD pattern which comprises one, two or more of the form-specific peaks, as listed in Table A2, below.

TABLE A2

Form-specific pXRD peaks, Form A

| Position °2θ | d-spacing (Å) | Overlaps w/Form |
| --- | --- | --- |
| 6.46 ± 0.10 | 13.679 ± 0.215 | H |
| 8.47 ± 0.10 | 10.442 ± 0.125 | H, J |
| 9.02 ± 0.10 | 9.803 ± 0.110 | B |

Crystalline Form B

Figure 2:
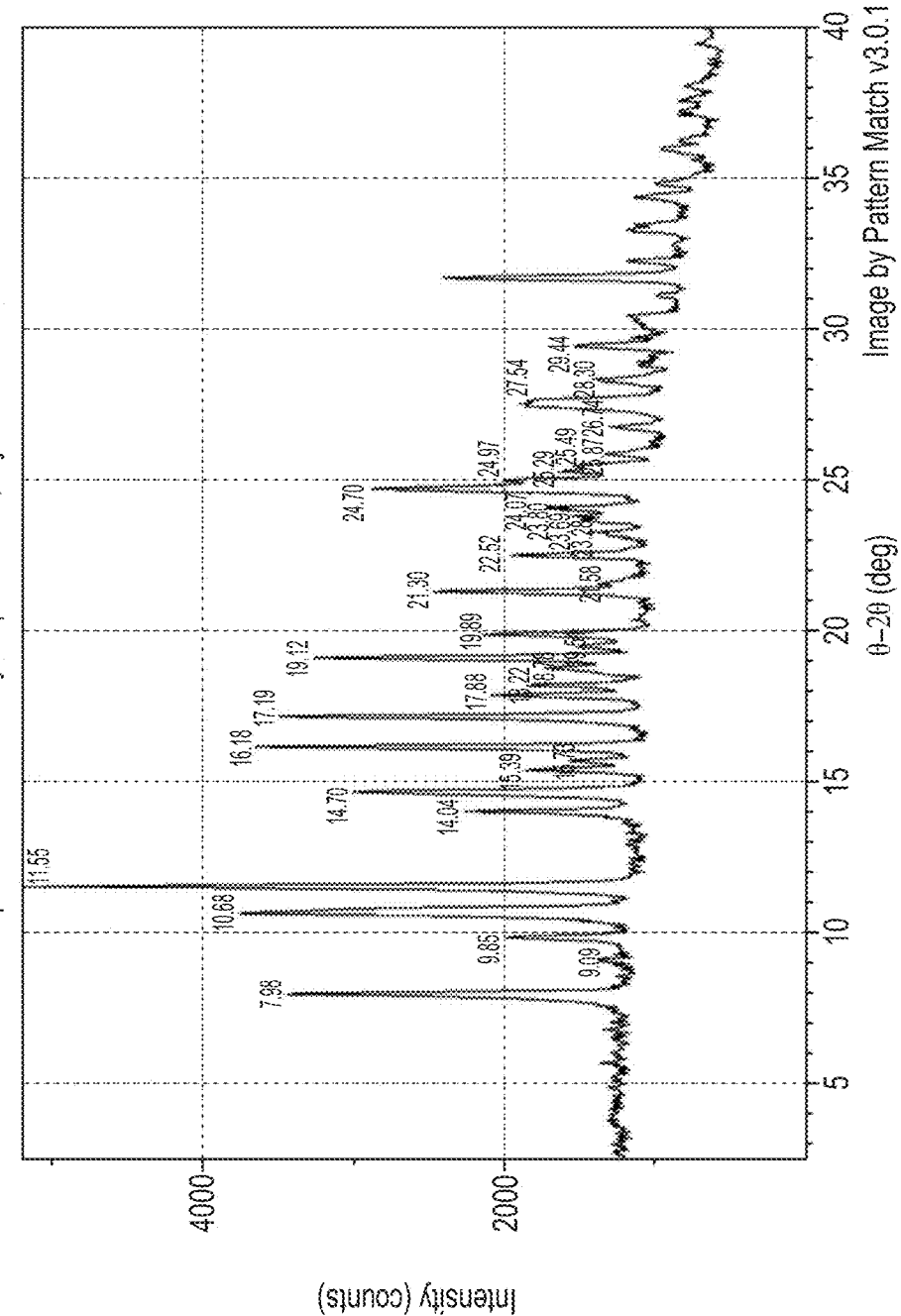
FIG. 2 illustrates a powder X-ray diffraction pattern of oxymorphone HCl crystalline Form B, expressed in terms of °2θ.

A representative sample of oxymorphone HCl crystalline Form B was analyzed using the INEL diffractometer as described above. Form B may be characterized by its pXRD peaks, as listed in Table B1, below. FIG. 2 illustrates a representative pXRD pattern for a representative sample of oxymorphone HCl crystalline form B.

TABLE B1 pXRD Observed Peaks, Oxymorphone HCl, Form B

| Position °2θ (±0.10) | d space (Å) | Relative Intensity (%) |
|---|---|---|
| 7.98 | 11.074 ± 0.140 | 66 |
| 9.09 | 9.728 ± 0.108 | 25 |
| 9.85 | 8.978 ± 0.092 | 38 |
| 10.68 | 8.282 ± 0.078 | 72 |
| 11.55 | 7.664 ± 0.067 | 100 |
| 14.04 | 6.309 ± 0.045 | 44 |
| 14.70 | 6.028 ± 0.041 | 58 |
| 15.39 | 5.759 ± 0.037 | 36 |
| 15.73 | 5.633 ± 0.036 | 30 |
| 16.18 | 5.477 ± 0.034 | 70 |
| 17.19 | 5.160 ± 0.030 | 67 |
| 17.88 | 4.961 ± 0.028 | 40 |
| 18.22 | 4.868 ± 0.027 | 35 |
| 18.78 | 4.726 ± 0.025 | 33 |
| 19.12 | 4.641 ± 0.024 | 63 |
| 19.51 | 4.551 ± 0.023 | 29 |
| 19.89 | 4.465 ± 0.022 | 41 |
| 21.30 | 4.171 ± 0.019 | 47 |
| 21.58 | 4.118 ± 0.019 | 26 |
| 22.52 | 3.949 ± 0.017 | 37 |
| 23.28 | 3.821 ± 0.016 | 28 |
| 23.69 | 3.755 ± 0.016 | 29 |
| 23.80 | 3.739 ± 0.016 | 30 |
| 24.07 | 3.697 ± 0.015 | 33 |
| 24.70 | 3.605 ± 0.014 | 55 |
| 24.97 | 3.566 ± 0.014 | 39 |
| 25.29 | 3.522 ± 0.014 | 31 |
| 25.49 | 3.494 ± 0.014 | 30 |
| 25.87 | 3.444 ± 0.013 | 26 |
| 26.74 | 3.334 ± 0.012 | 25 |
| 27.54 | 3.239 ± 0.012 | 37 |
| 28.30 | 3.154 ± 0.011 | 26 |
| 29.44 | 3.034 ± 0.010 | 29 |

In an embodiment, crystalline Form B is characterized by its powder XRD pattern which comprises peaks having a relative intensity of greater than or equal to about 35%, preferably peaks having a relative intensity of greater than or equal to about 50%.

In another embodiment, oxymorphone HCl, crystalline Form B is characterized by its pXRD pattern which comprises two or more of the form-specific peaks, as listed in Table B2, below. Where an overlapping Form listed in the Table below appears in parentheses, said Form exhibits peaks which may or may not overlap, depending on the resolution of the measured pXRD pattern.

TABLE B2

Characteristic pXRD peaks, Form B

| Position °2θ | d-spacing (Å) | Overlaps w/Form |
|---|---|---|
| 7.98 ± 0.10 | 11.074 ± 0.140 | C, G, H, (J), K |
| 9.85 ± 0.10 | 8.978 ± 0.092 | F, G, L |
| 10.68 ± 0.10 | 8.282 ± 0.078 | C, D, F |
| 11.55 ± 0.10 | 7.664 ± 0.067 | A, C, (D), M |
| 14.70 ± 0.10 | 6.028 ± 0.041 | D, F |

Crystalline Form C

Figure 3:
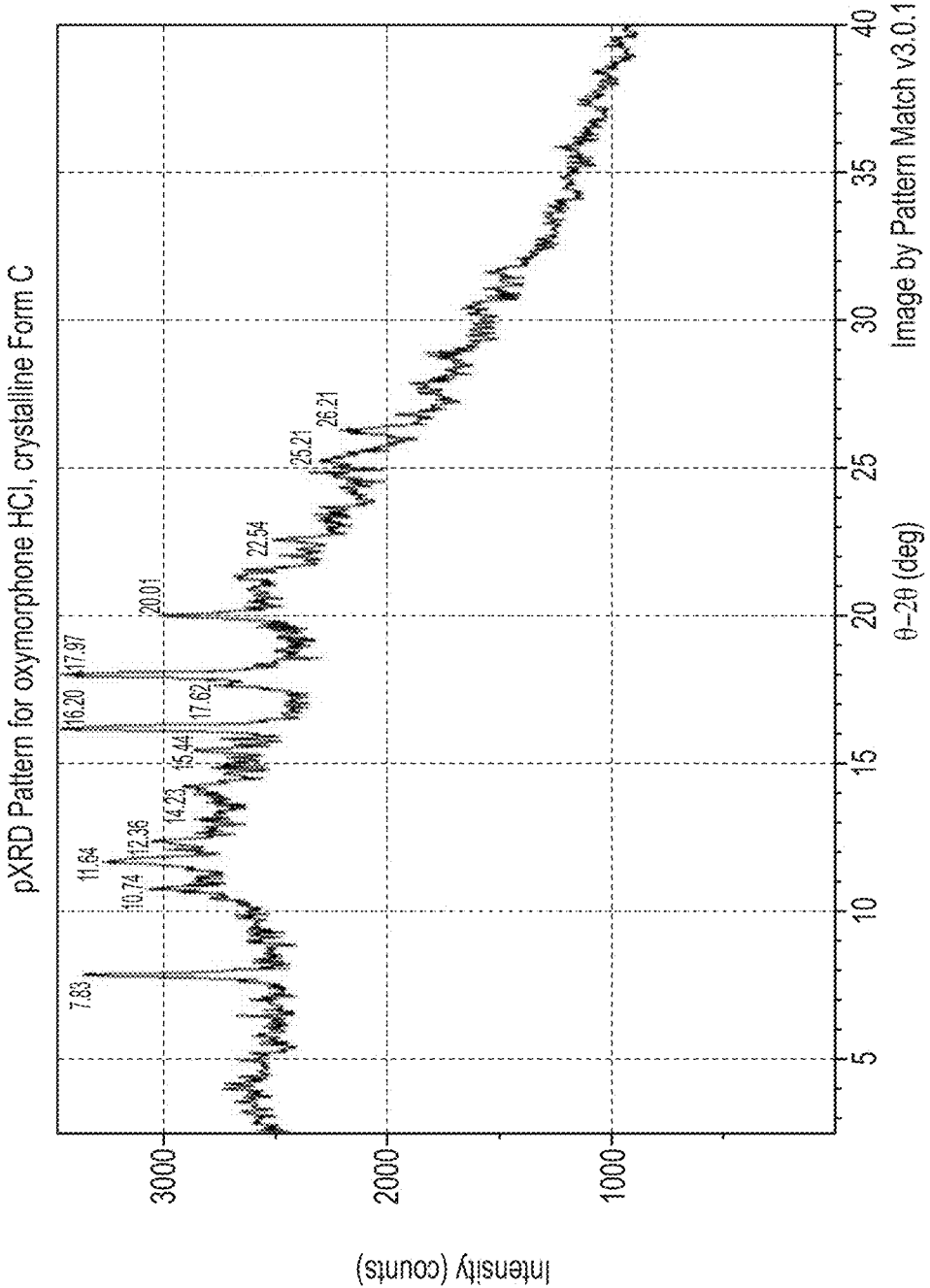
FIG. 3 illustrates a powder X-ray diffraction pattern of oxymorphone HCl crystalline Form C, expressed in terms of °2θ.

A representative sample of oxymorphone HCl crystalline Form C was analyzed using the INEL diffractometer as described above. Form C may be characterized by its pXRD peaks, as listed in Table C1, below. FIG. 3 illustrates a representative pXRD pattern for a representative sample of oxymorphone HCl crystalline form C.

TABLE C1 pXRD Observed Peaks, Oxymorphone HCl, Form C

| Position °2θ (± 0.10) | d space (Å) | Relative Intensity (%) |
|---|---|---|
| 7.83 | 11.291 ± 0.146 | 96 |
| 10.74 | 8.241 ± 0.077 | 90 |
| 11.64 | 7.606 ± 0.066 | 94 |
| 12.31 | 7.190 ± 0.058 | 89 |
| 14.23 | 6.224 ± 0.044 | 85 |
| 15.44 | 5.738 ± 0.037 | 83 |
| 16.20 | 5.470 ± 0.034 | 100 |
| 17.62 | 5.033 ± 0.028 | 81 |
| 17.97 | 4.937 ± 0.027 | 98 |
| 20.01 | 4.437 ± 0.022 | 87 |
| 22.54 | 3.945 ± 0.017 | 73 |
| 25.21 | 3.533 ± 0.014 | 68 |
| 26.21 | 3.400 ± 0.013 | 63 |

In an embodiment, crystalline Form C is characterized by its powder XRD pattern which comprises peaks having a relative intensity of greater than or equal to about 80%, preferably peaks having a relative intensity of greater than or equal to about 90%.

In another embodiment, oxymorphone HCl, crystalline Form C is characterized by its pXRD pattern which comprises two or more of the form-specific peaks, as listed in Table C2, below. Where an overlapping Form listed in the Table below appears in parentheses, said Form exhibits peaks which may or may not overlap, depending on the resolution of the measured pXRD pattern.

TABLE C2

Form-specific pXRD peaks, Form C

| position °2θ | d-spacing (Å) | Overlaps w/Form |
|---|---|---|
| 7.83 ± 0.10 | 11.291 ± 0.146 | B, H, J |
| 12.31 ± 0.10 | 7.190 ± 0.058 | D, G, (K, L) |

Crystalline Form D

Figure 4:
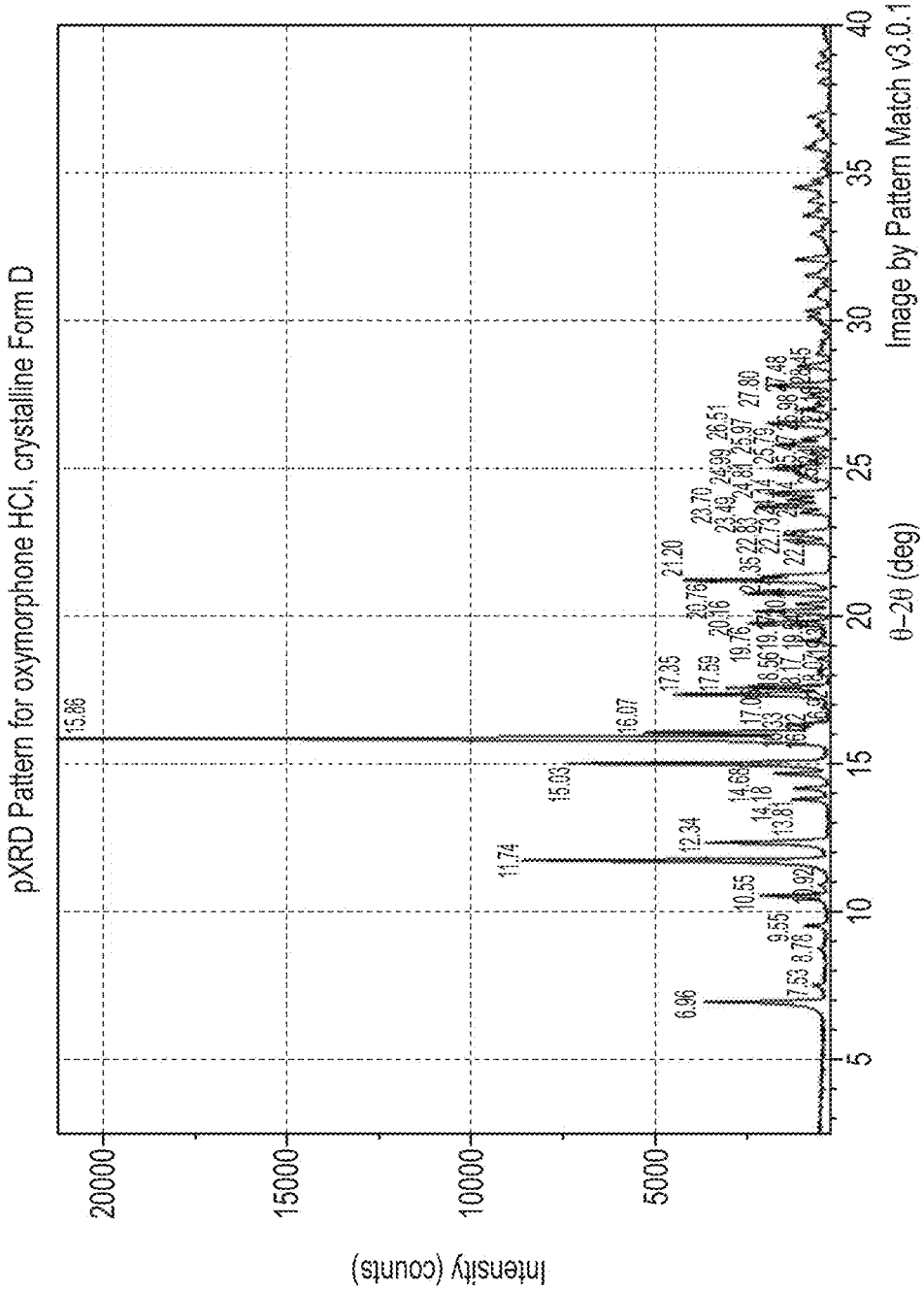
FIG. 4 illustrates a powder X-ray diffraction pattern of oxymorphone HCl crystalline Form D, expressed in terms of °2θ.

A representative sample of oxymorphone HCl crystalline Form D was analyzed using the PANalytical diffractometer as described above. Form D may be characterized by its pXRD peaks, as listed in Table D1, below. FIG. 4 illustrates a representative pXRD pattern for a representative sample of oxymorphone HCl crystalline form D.

TABLE D1 pXRD Observed Peaks, Oxymorphone HCl, Form D

| Position °2θ (±0.10) | d space (Å) | Relative Intensity (%) |
|---|---|---|
| 6.96 | 12.705 ± 0.185 | 17 |
| 7.53 | 11.747 ± 0.158 | 3 |
| 8.78 | 10.073 ± 0.116 | 3 |
| 9.55 | 9.263 ± 0.098 | 5 |
| 10.55 | 8.385 ± 0.080 | 10 |
| 10.92 | 8.104 ± 0.075 | 3 |
| 11.74 | 7.540 ± 0.065 | 40 |
| 12.34 | 7.174 ± 0.058 | 17 |
| 13.81 | 6.413 ± 0.047 | 6 |
| 14.18 | 6.247 ± 0.044 | 6 |
| 14.68 | 6.035 ± 0.041 | 8 |
| 15.03 | 5.895 ± 0.039 | 35 |
| 15.86 | 5.586 ± 0.035 | 100 |
| 16.07 | 5.517 ± 0.034 | 25 |
| 16.22 | 5.466 ± 0.034 | 5 |
| 16.33 | 5.427 ± 0.033 | 7 |
| 16.92 | 5.241 ± 0.031 | 2 |
| 17.05 | 5.200 ± 0.03 | 2 |

TABLE D1-continued

| Position °2θ (±0.10) | d space (Å) | Relative Intensity (%) |
|---|---|---|
| 17.35 | 5.111 ± 0.029 | 21 |
| 17.59 | 5.043 ± 0.029 | 14 |
| 18.07 | 4.909 ± 0.027 | 3 |
| 18.17 | 4.882 ± 0.027 | 3 |
| 18.56 | 4.782 ± 0.026 | 3 |
| 19.17 | 4.629 ± 0.024 | 5 |
| 19.37 | 4.582 ± 0.024 | 3 |
| 19.54 | 4.543 ± 0.023 | 3 |
| 19.76 | 4.493 ± 0.023 | 12 |
| 20.16 | 4.405 ± 0.022 | 11 |
| 20.41 | 4.351 ± 0.021 | 6 |
| 20.76 | 4.279 ± 0.020 | 12 |
| 21.20 | 4.192 ± 0.020 | 20 |
| 21.35 | 4.163 ± 0.019 | 10 |
| 22.48 | 3.955 ± 0.017 | 6 |
| 22.73 | 3.912 ± 0.017 | 7 |
| 22.83 | 3.895 ± 0.017 | 6 |
| 23.49 | 3.788 ± 0.016 | 5 |
| 23.70 | 3.754 ± 0.016 | 11 |
| 23.94 | 3.718 ± 0.015 | 7 |
| 24.14 | 3.687 ± 0.015 | 9 |
| 24.81 | 3.589 ± 0.014 | 6 |
| 24.99 | 3.563 ± 0.014 | 9 |
| 25.24 | 3.529 ± 0.014 | 4 |
| 25.47 | 3.497 ± 0.014 | 4 |
| 25.79 | 3.454 ± 0.013 | 8 |
| 25.97 | 3.430 ± 0.013 | 5 |
| 26.51 | 3.362 ± 0.013 | 9 |
| 26.98 | 3.305 ± 0.012 | 6 |
| 27.18 | 3.281 ± 0.012 | 3 |
| 27.48 | 3.246 ± 0.012 | 4 |
| 27.80 | 3.210 ± 0.011 | 10 |
| 28.45 | 3.138 ± 0.011 | 5 |

In an embodiment, crystalline Form D is characterized by its powder XRD pattern which comprises peaks having a relative intensity of greater than or equal to about 5%, preferably peaks having a relative intensity of greater than or equal to about 10%.

In another embodiment, oxymorphone HCl, crystalline Form D is characterized by its pXRD pattern which comprises the single form-specific peak at 6.96±0.10°2θ. In another embodiment, oxymorphone HCl, crystalline Form D is characterized by its pXRD pattern which comprises two or more of the form-specific peaks, as listed in Table D2, below.

TABLE D2

Form-specific pXRD peaks, Form D

| Position °2θ | d-spacing (Å) | Overlaps w/Form |
|---|---|---|
| 6.96 ± 0.10 | 12.705 ± 0.185 | none |
| 10.55 ± 0.10 | 8.385 ± 0.080 | B, C, F, H, J |
| 12.34 ± 0.10 | 7.174 ± 0.058 | C, G, K |
| 15.03 ± 0.10 | 5.895 ± 0.039 | H, L, M |

Crystalline Form F

Figure 5:
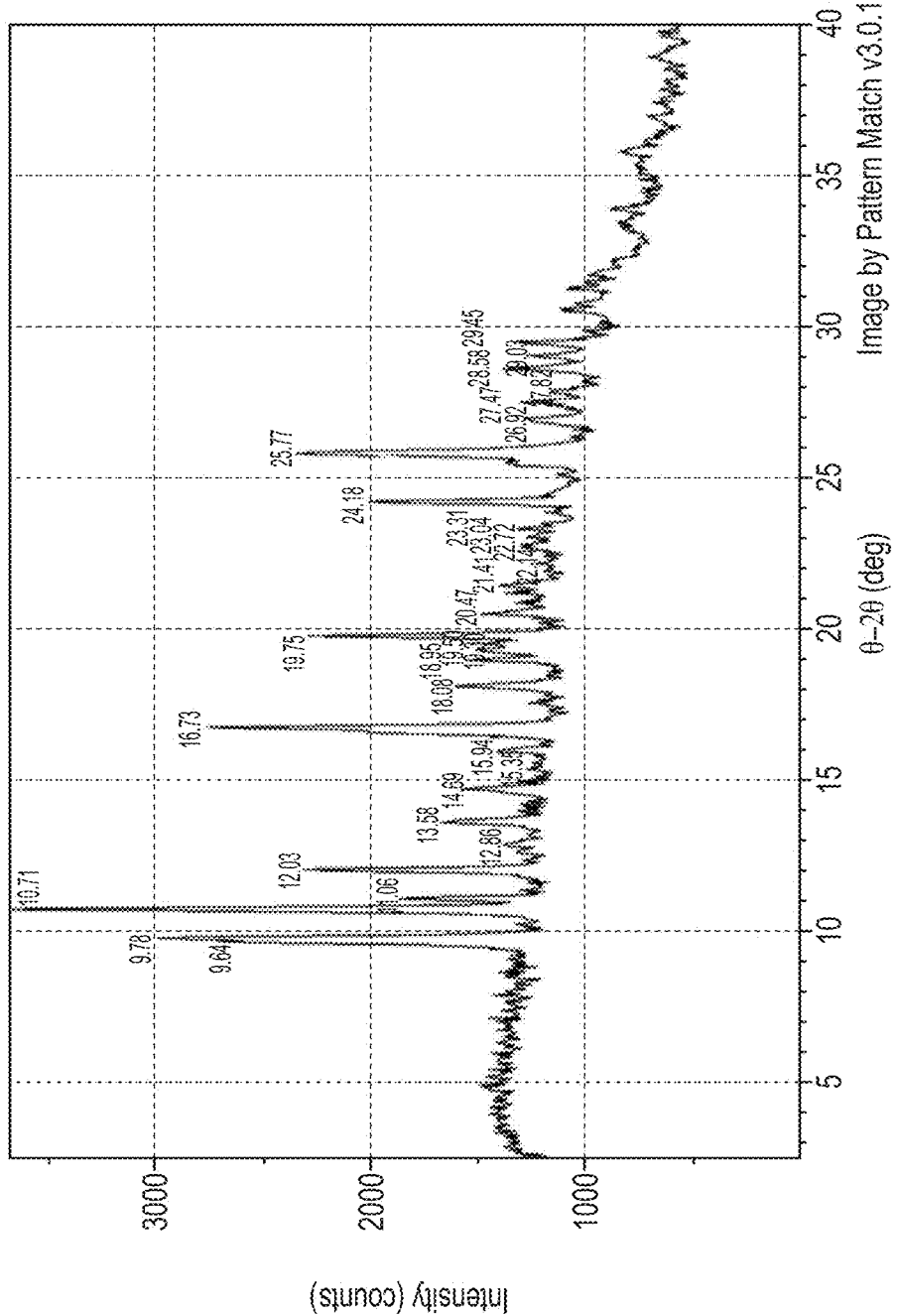
FIG. 5 illustrates a powder X-ray diffraction pattern of oxymorphone HCl crystalline Form F, expressed in terms of °2θ.

A representative sample of oxymorphone HCl crystalline Form F was analyzed using the Inel diffractometer as described above. Form F may be characterized by its pXRD peaks, as listed in Table F1, below. FIG. 5 illustrates a representative pXRD pattern for a representative sample of oxymorphone HCl crystalline form F.

TABLE F1 pXRD Observed Peaks, Oxymorphone HCl, Form F

| Position °2θ (±0.15) | d space (Å) | Relative Intensity (%) |
|---|---|---|
| 9.78 | 9.045 ± 0.136 | 81 |
| 10.71 | 8.258 ± 0.117 | 100 |
| 11.06 | 8.001 ± 0.110 | 51 |
| 12.03 | 7.358 ± 0.093 | 63 |
| 12.86 | 6.885 ± 0.081 | 37 |
| 13.58 | 6.518 ± 0.072 | 45 |
| 14.69 | 6.029 ± 0.062 | 43 |
| 15.35 | 5.772 ± 0.057 | 35 |
| 15.94 | 5.561 ± 0.052 | 38 |
| 16.73 | 5.298 ± 0.048 | 75 |
| 18.08 | 4.905 ± 0.041 | 43 |
| 18.95 | 4.683 ± 0.037 | 42 |
| 19.30 | 4.600 ± 0.036 | 41 |
| 19.50 | 4.551 ± 0.035 | 41 |
| 19.75 | 4.496 ± 0.034 | 62 |
| 20.47 | 4.338 ± 0.032 | 40 |
| 21.41 | 4.151 ± 0.029 | 38 |
| 22.14 | 4.016 ± 0.027 | 34 |
| 22.72 | 3.913 ± 0.026 | 34 |
| 23.04 | 3.861 ± 0.025 | 35 |
| 23.31 | 3.816 ± 0.024 | 36 |
| 24.18 | 3.681 ± 0.023 | 54 |
| 25.77 | 3.457 ± 0.020 | 64 |
| 26.92 | 3.313 ± 0.018 | 34 |
| 27.47 | 3.247 ± 0.017 | 36 |
| 27.82 | 3.207 ± 0.017 | 31 |
| 28.58 | 3.123 ± 0.016 | 37 |
| 29.03 | 3.076 ± 0.016 | 34 |
| 29.45 | 3.033 ± 0.015 | 35 |

In an embodiment, crystalline Form F is characterized by its powder XRD pattern which comprises peaks having a relative intensity of greater than or equal to about 40%, preferably peaks having a relative intensity of greater than or equal to about 50%.

In another embodiment, oxymorphone HCl, crystalline Form F is characterized by its pXRD pattern which comprises two or more of the form-specific peaks, as listed in Table F2, below.

TABLE F2

Form-specific pXRD peaks, Form F

| position °2θ | d-spacing (Å) | Overlaps w/Form |
|---|---|---|
| 9.78 ± 0.15 | 9.045 ± 0.093 | B, G, L |
| 10.71 ± 0.15 | 8.258 ± 0.078 | B, C, D |
| 11.06 ± 0.15 | 8.001 ± 0.073 | J, L |
| 12.03 ± 0.10 | 7.358 ± 0.061 | A, H, J |

Crystalline Form G

Figure 6:
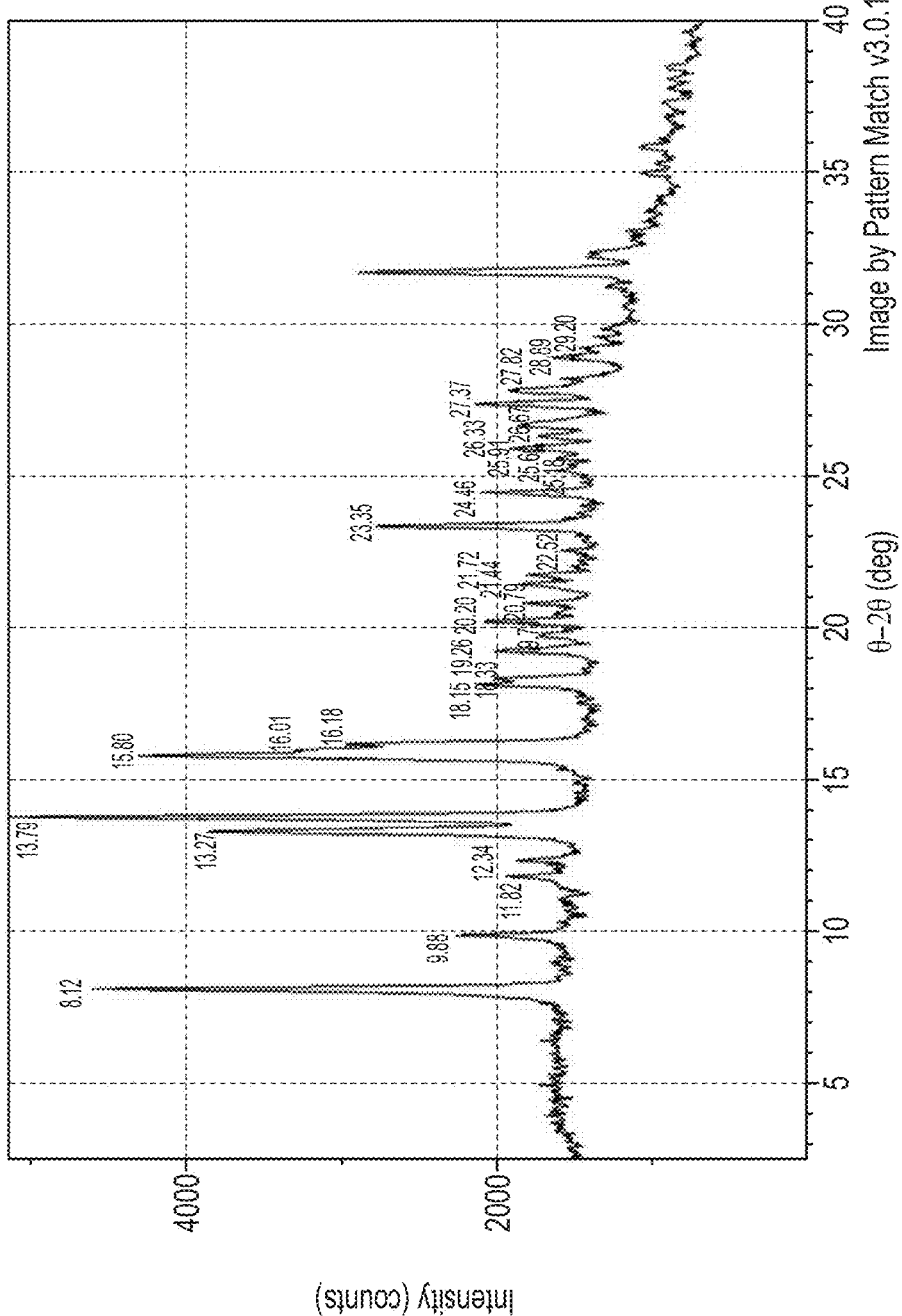
FIG. 6 illustrates a powder X-ray diffraction pattern of oxymorphone HCl crystalline Form G, expressed in terms of °2θ.

A representative sample of oxymorphone HCl crystalline Form G was analyzed using the INEL diffractometer as described above. Form G may be characterized by its pXRD peaks, as listed in Table G1, below. FIG. 6 illustrates a representative pXRD pattern for a representative sample of oxymorphone HCl crystalline form G.

TABLE G1 pXRD Observed Peaks, Oxymorphone HCl, Form G

| Position °2θ (±0.10) | d space (Å) | Relative Intensity (%) |
|---|---|---|
| 8.12 | 10.892 ± 0.136 | 89 |
| 9.88 | 8.950 ± 0.091 | 44 |
| 11.82 | 7.487 ± 0.064 | 37 |
| 12.34 | 7.173 ± 0.058 | 36 |

TABLE G1-continued pXRD Observed Peaks, Oxymorphone HCl, Form G

| Position °2θ (±0.10) | d space (Å) | Relative Intensity (%) |
|---|---|---|
| 13.27 | 6.670 ± 0.050 | 75 |
| 13.79 | 6.421 ± 0.047 | 100 |
| 15.80 | 5.609 ± 0.036 | 83 |
| 16.01 | 5.537 ± 0.035 | 64 |
| 16.18 | 5.478 ± 0.034 | 57 |
| 18.15 | 4.887 ± 0.027 | 41 |
| 18.33 | 4.841 ± 0.026 | 39 |
| 19.26 | 4.608 ± 0.024 | 38 |
| 19.71 | 4.504 ± 0.023 | 33 |
| 20.20 | 4.397 ± 0.022 | 40 |
| 20.79 | 4.274 ± 0.020 | 35 |
| 21.44 | 4.144 ± 0.019 | 36 |
| 21.72 | 4.092 ± 0.019 | 35 |
| 22.52 | 3.949 ± 0.017 | 30 |
| 23.35 | 3.810 ± 0.016 | 54 |
| 24.46 | 3.640 ± 0.015 | 41 |
| 25.18 | 3.536 ± 0.014 | 31 |
| 25.60 | 3.480 ± 0.013 | 31 |
| 25.91 | 3.439 ± 0.013 | 37 |
| 26.33 | 3.385 ± 0.013 | 34 |
| 26.67 | 3.342 ± 0.012 | 35 |
| 27.37 | 3.259 ± 0.012 | 41 |
| 27.82 | 3.207 ± 0.011 | 36 |
| 28.89 | 3.090 ± 0.011 | 31 |
| 29.20 | 3.058 ± 0.010 | 28 |

In an embodiment, crystalline Form G is characterized by its powder XRD pattern which comprises peaks having a relative intensity of greater than or equal to about 35%, preferably peaks having a relative intensity of greater than or equal to about 50%.

In another embodiment, oxymorphone HCl, crystalline Form G is characterized by its pXRD pattern which comprises two or more of the form-specific peaks, as listed in Table G2, below. Where an overlapping Form listed in the Table below appears in parentheses, said Form exhibits peaks which may or may not overlap, depending on the resolution of the measured pXRD pattern.

TABLE G2

Form-specific pXRD peaks, Form G

| position °2θ | d-spacing (Å) | Overlaps w/Form |
|---|---|---|
| 8.12 ± 0.10 | 10.892 ± 0.136 | B, K |
| 9.88 ± 0.10 | 8.950 ± 0.091 | B, F, L |
| 13.27 ± 0.10 | 6.670 ± 0.050 | C, H, L, (M) |
| 13.79 ± 0.10 | 6.421 ± 0.047 | D |

Crystalline Form H

Figure 7:
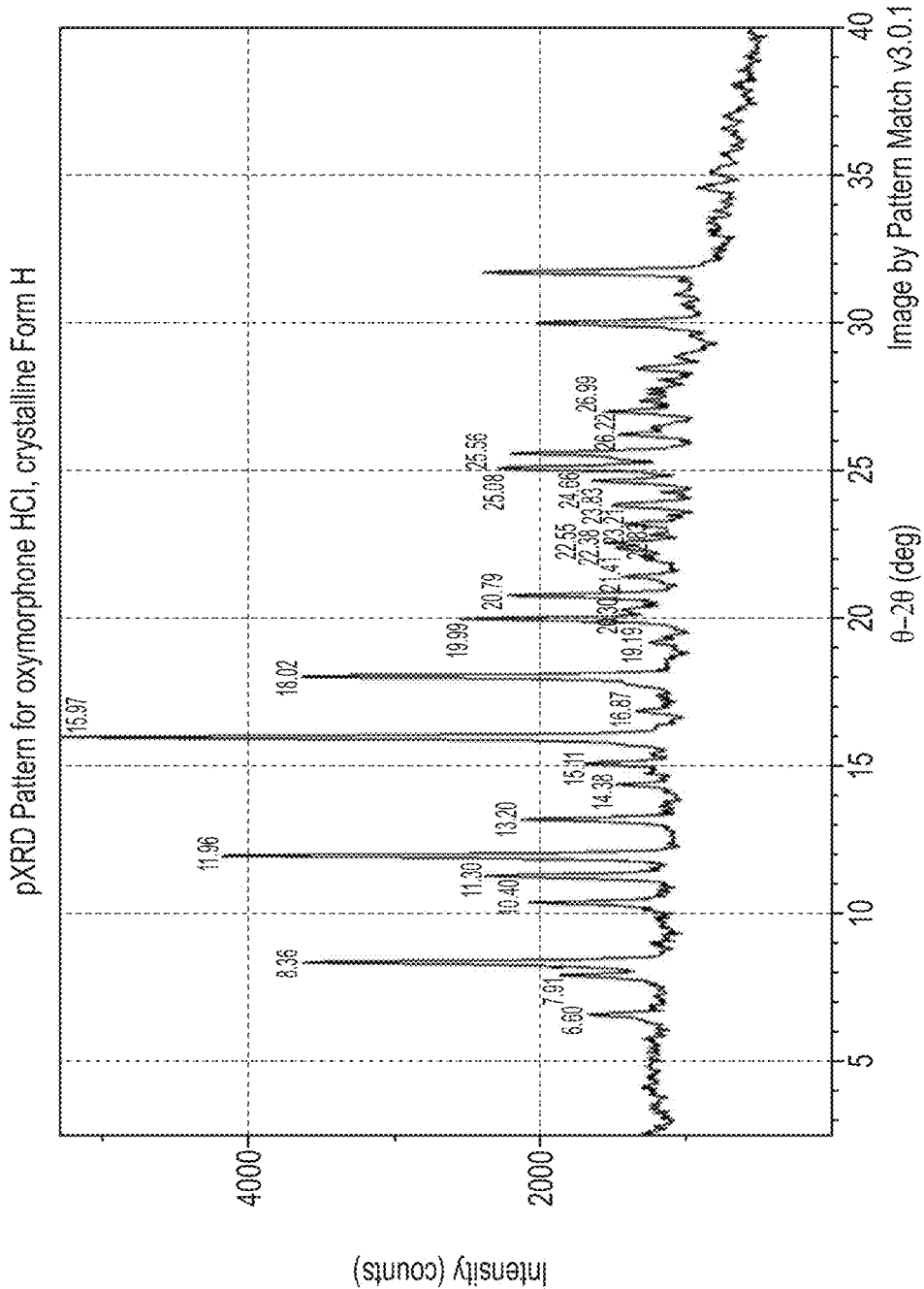
FIG. 7 illustrates a powder X-ray diffraction pattern of oxymorphone HCl crystalline Form H, expressed in terms of °2θ.

A representative sample of oxymorphone HCl crystalline Form H was analyzed using the INEL diffractometer as described above. Form H may be characterized by its pXRD peaks, as listed in Table H1, below. FIG. 7 illustrates a representative pXRD pattern for a representative sample of oxymorphone HCl crystalline form H.

TABLE H1 pXRD Observed Peaks, Oxymorphone HCl, Form H

| Position °2θ (±0.10) | d space (Å) | Relative Intensity (%) |
|---|---|---|
| 6.60 | 13.401 ± 0.206 | 32 |
| 7.91 | 11.177 ± 0.143 | 35 |
| 8.36 | 10.577 ± 0.128 | 69 |
| 10.40 | 8.505 ± 0.082 | 39 |

TABLE H1-continued pXRD Observed Peaks, Oxymorphone HCl, Form H

| Position °2θ (±0.10) | d space (Å) | Relative Intensity (%) |
|---|---|---|
| 11.30 | 7.830 ± 0.070 | 45 |
| 11.96 | 7.401 ± 0.062 | 79 |
| 13.20 | 6.705 ± 0.051 | 40 |
| 14.38 | 6.159 ± 0.043 | 28 |
| 15.11 | 5.864 ± 0.039 | 32 |
| 15.97 | 5.549 ± 0.035 | 100 |
| 16.87 | 5.255 ± 0.031 | 25 |
| 18.02 | 4.924 ± 0.027 | 68 |
| 19.19 | 4.625 ± 0.024 | 24 |
| 19.99 | 4.442 ± 0.022 | 48 |
| 20.30 | 4.375 ± 0.021 | 27 |
| 20.79 | 4.274 ± 0.020 | 42 |
| 21.41 | 4.151 ± 0.019 | 27 |
| 22.38 | 3.973 ± 0.018 | 28 |
| 22.55 | 3.943 ± 0.017 | 29 |
| 22.83 | 3.896 ± 0.017 | 23 |
| 23.21 | 3.832 ± 0.016 | 27 |
| 23.83 | 3.734 ± 0.016 | 28 |
| 24.66 | 3.610 ± 0.014 | 31 |
| 25.08 | 3.551 ± 0.014 | 43 |
| 25.56 | 3.484 ± 0.013 | 42 |
| 26.22 | 3.398 ± 0.013 | 28 |
| 26.99 | 3.304 ± 0.012 | 30 |

In an embodiment, crystalline Form H is characterized by its powder XRD pattern which comprises peaks having a relative intensity of greater than or equal to about 25%, preferably peaks having a relative intensity of greater than or equal to about 40%.

In another embodiment, oxymorphone HCl, crystalline Form H is characterized by its pXRD pattern which comprises two or more of the form-specific peaks, as listed in Table H2, below.

TABLE H2

Characteristic pXRD peaks, Form H

| position °2θ | d-spacing (Å) | Overlaps w/Form |
|---|---|---|
| 6.60 ± 0.10 | 13.401 ± 0.206 | A |
| 7.91 ± 0.10 | 11.177 ± 0.143 | B, C, J, K |
| 11.30 ± 0.10 | 7.830 ± 0.070 | L, M |

Crystalline Form J

Figure 8:
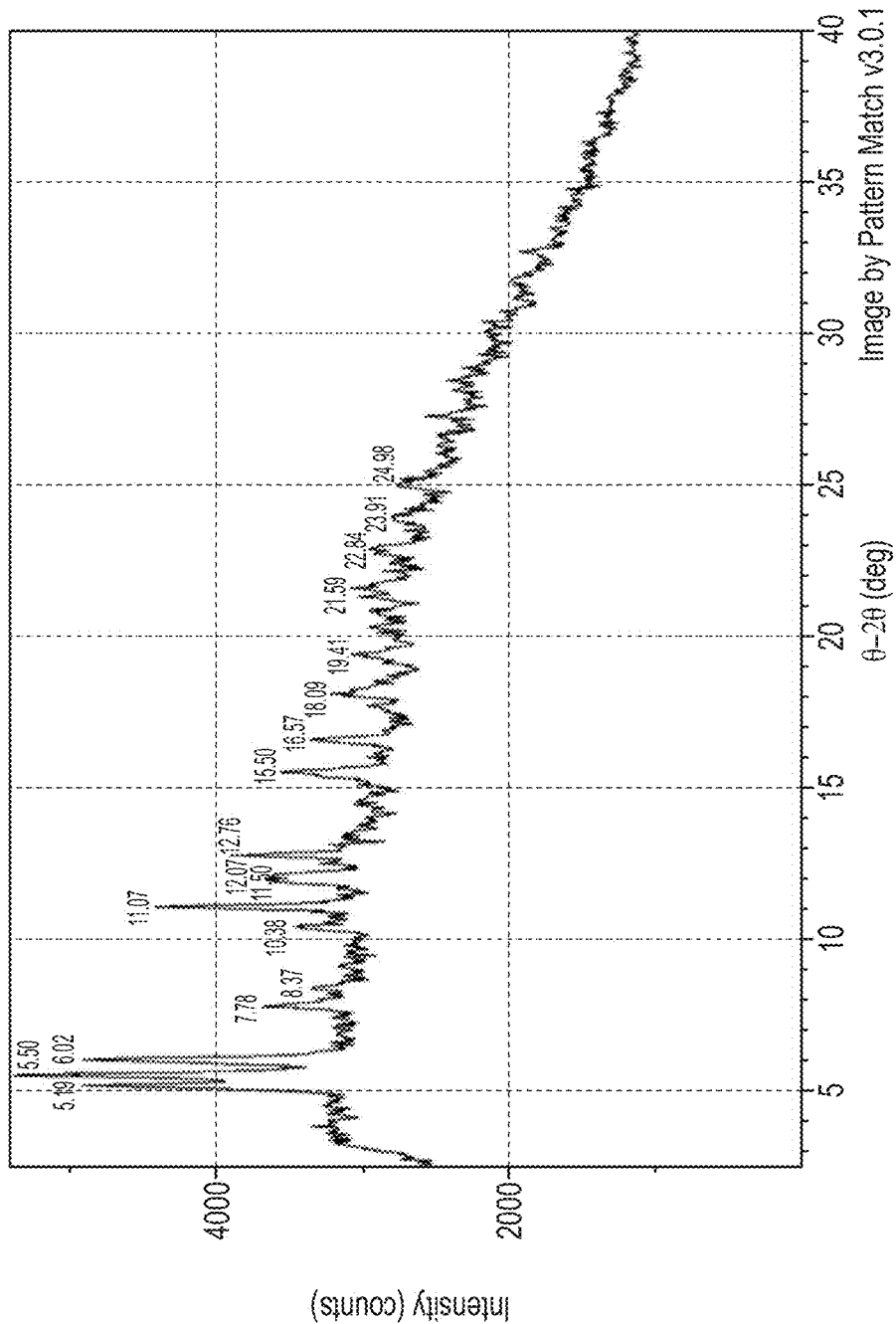
FIG. 8 illustrates a powder X-ray diffraction pattern of oxymorphone HCl crystalline Form J, expressed in terms of °2θ.

A representative sample of oxymorphone HCl crystalline Form J was analyzed using the INEL diffractometer as described above. Form J may be characterized by its pXRD peaks, as listed in Table J1, below. FIG. 8 illustrates a representative pXRD pattern for a representative sample of oxymorphone HCl crystalline form J.

TABLE J1 pXRD Observed Peaks, Oxymorphone HCl, Form J

| Position °2θ (±0.10) | d space (Å) | Relative Intensity (%) |
|---|---|---|
| 5.19 | 17.032 ± 0.334 | 91 |
| 5.50 | 16.069 ± 0.297 | 100 |
| 6.02 | 14.685 ± 0.248 | 91 |
| 7.78 | 11.360 ± 0.148 | 68 |
| 8.37 | 10.563 ± 0.127 | 62 |
| 10.38 | 8.525 ± 0.083 | 63 |
| 11.07 | 7.994 ± 0.073 | 81 |
| 11.90 | 7.438 ± 0.063 | 68 |
| 12.07 | 7.332 ± 0.061 | 68 |
| 12.76 | 6.936 ± 0.055 | 72 |
| 15.50 | 5.718 ± 0.037 | 66 |

TABLE J1-continued pXRD Observed Peaks, Oxymorphone HCl, Form J

| Position °2θ (±0.10) | d space (Å) | Relative Intensity (%) |
|---|---|---|
| 16.57 | 5.350 ± 0.032 | 62 |
| 18.09 | 4.903 ± 0.027 | 59 |
| 19.41 | 4.574 ± 0.023 | 57 |
| 21.59 | 4.116 ± 0.019 | 57 |
| 22.84 | 3.894 ± 0.017 | 54 |
| 23.91 | 3.722 ± 0.015 | 52 |
| 24.98 | 3.564 ± 0.014 | 51 |

In an embodiment, crystalline Form J is characterized by its powder XRD pattern which comprises peaks having a relative intensity of greater than or equal to about 60%, preferably peaks having a relative intensity of greater than or equal to about 80%.

In another embodiment, oxymorphone HCl, crystalline Form J is characterized by its pXRD pattern which comprises the single form-specific peak at 5.19±0.10°2θ. In another embodiment, oxymorphone HCl, crystalline Form J is characterized by its pXRD pattern which comprises the single form-specific peak at 6.02±0.10°2θ. In another embodiment, oxymorphone HCl, crystalline Form J is characterized by its pXRD pattern which comprises two or more of the form-specific peaks, as listed in Table J2, below. Where an overlapping Form listed in the Table below appears in parentheses, said Form exhibits peaks which may or may not overlap, depending on the resolution of the measured pXRD pattern.

TABLE J2

Form-specific pXRD peaks, Form J

| position °2θ | d-spacing (Å) | Overlaps w/Form |
|---|---|---|
| 5.19 ± 0.10 | 17.032 ± 0.334 | None |
| 5.50 ± 0.10 | 16.069 ± 0.297 | (M) |
| 6.02 ± 0.10 | 14.685 ± 0.248 | None |
| 11.07 ± 0.10 | 7.994 ± 0.073 | (D), F, L |

Crystalline Form K

Figure 9:
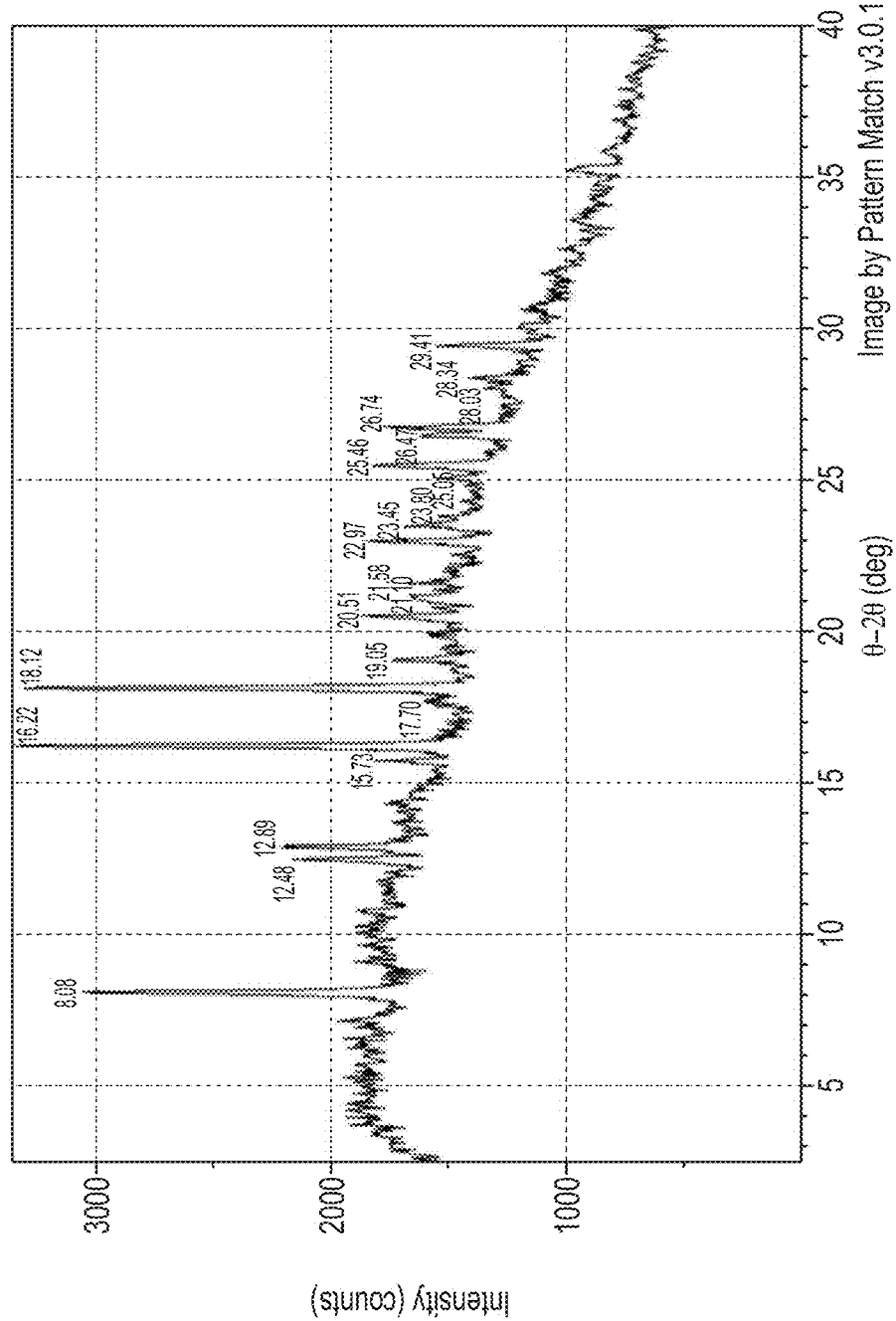
FIG. 9 illustrates a powder X-ray diffraction pattern of oxymorphone HCl crystalline Form K, expressed in terms of °2θ.

A representative sample of oxymorphone HCl crystalline Form K was analyzed using the INEL diffractometer as described above. Form K may be characterized by its pXRD peaks, as listed in Table K1, below. FIG. 9 illustrates a representative pXRD pattern for a representative sample of oxymorphone HCl crystalline form K.

TABLE K1 pXRD Observed Peaks, Oxymorphone HCl, Form K

| Position °2θ (±0.10) | d space (Å) | Relative Intensity (%) |
|---|---|---|
| 8.08 | 10.938 ± 0.137 | 89 |
| 12.48 | 7.094 ± 0.057 | 64 |
| 12.89 | 6.867 ± 0.053 | 66 |
| 15.73 | 5.634 ± 0.036 | 54 |
| 16.22 | 5.466 ± 0.034 | 100 |
| 17.70 | 5.010 ± 0.028 | 46 |
| 18.12 | 4.896 ± 0.027 | 98 |
| 19.05 | 4.658 ± 0.024 | 52 |
| 20.51 | 4.331 ± 0.021 | 55 |
| 21.10 | 4.211 ± 0.020 | 49 |
| 21.58 | 4.118 ± 0.019 | 49 |
| 22.97 | 3.872 ± 0.017 | 55 |
| 23.45 | 3.793 ± 0.016 | 50 |
| 23.80 | 3.739 ± 0.016 | 46 |
| 25.05 | 3.556 ± 0.014 | 45 |
| 25.46 | 3.498 ± 0.014 | 54 |

TABLE K1-continued pXRD Observed Peaks, Oxymorphone HCl, Form K

| Position °2θ (±0.10) | d space (Å) | Relative Intensity (%) |
|---|---|---|
| 26.47 | 3.368 ± 0.013 | 48 |
| 26.74 | 3.334 ± 0.012 | 53 |
| 28.03 | 3.184 ± 0.011 | 40 |
| 28.34 | 3.150 ± 0.011 | 42 |
| 29.41 | 3.037 ± 0.010 | 46 |

In an embodiment, crystalline Form K is characterized by its powder XRD pattern which comprises peaks having a relative intensity of greater than or equal to about 50%, preferably peaks having a relative intensity of greater than or equal to about 65%.

In another embodiment, oxymorphone HCl, crystalline Form K is characterized by its pXRD pattern which comprises two or more of the form-specific peaks, as listed in Table GK2, below. Where an overlapping Form listed in the Table below appears in parentheses, said Form exhibits peaks which may or may not overlap, depending on the resolution of the measured pXRD pattern.

TABLE K2

Form-specific pXRD peaks, Form K

| position °2θ | d-spacing (Å) | Overlaps w/Form |
|---|---|---|
| 8.08 ± 0.10 | 10.938 ± 0.137 | B, G, H |
| 12.48 ± 0.10 | 7.094 ± 0.057 | (C), D, G, L |
| 12.89 ± 0.10 | 6.867 ± 0.053 | A, F, J, M |

Crystalline Form L

Figure 10:
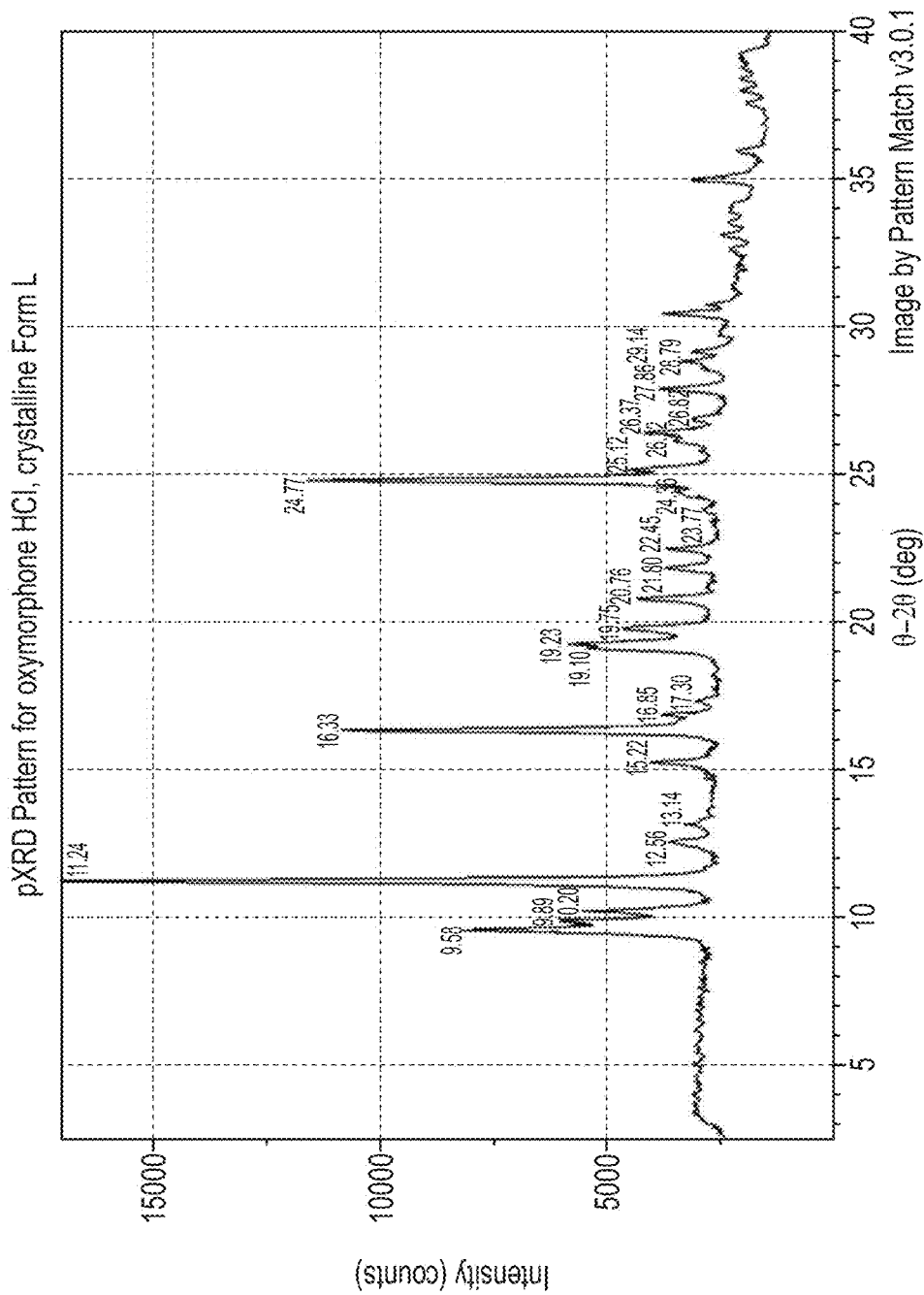
FIG. 10 illustrates a powder X-ray diffraction pattern of oxymorphone HCl crystalline Form L, expressed in terms of °2θ.

A representative sample of oxymorphone HCl crystalline Form L was analyzed using the INEL diffractometer as described above. Form L may be characterized by its pXRD peaks, as listed in Table L1, below. FIG. 10 illustrates a representative pXRD pattern for a representative sample of oxymorphone HCl crystalline form L.

TABLE L1 pXRD Observed Peaks, Oxymorphone HCl, Form L

| Position °2θ (±0.10) | d space (Å) | Relative Intensity (%) |
|---|---|---|
| 9.58 | 9.231 ± 0.097 | 48 |
| 9.89 | 8.941 ± 0.091 | 35 |
| 10.20 | 8.669 ± 0.086 | 32 |
| 11.24 | 7.871 ± 0.070 | 100 |
| 12.56 | 7.050 ± 0.056 | 21 |
| 13.14 | 6.736 ± 0.051 | 19 |
| 15.22 | 5.821 ± 0.038 | 24 |
| 16.33 | 5.429 ± 0.033 | 64 |
| 16.85 | 5.263 ± 0.031 | 22 |
| 17.30 | 5.127 ± 0.030 | 18 |
| 19.10 | 4.648 ± 0.024 | 32 |
| 19.23 | 4.615 ± 0.024 | 34 |
| 19.75 | 4.494 ± 0.023 | 27 |
| 20.76 | 4.279 ± 0.020 | 26 |
| 21.80 | 4.078 ± 0.019 | 22 |
| 22.45 | 3.960 ± 0.017 | 22 |
| 23.77 | 3.743 ± 0.016 | 17 |
| 24.36 | 3.654 ± 0.015 | 20 |
| 24.77 | 3.594 ± 0.014 | 68 |
| 25.12 | 3.545 ± 0.014 | 27 |
| 26.12 | 3.411 ± 0.013 | 21 |
| 26.37 | 3.380 ± 0.013 | 24 |

TABLE L1-continued pXRD Observed Peaks, Oxymorphone HCl, Form L

| Position °2θ (±0.10) | d space (Å) | Relative Intensity (%) |
|---|---|---|
| 26.82 | 3.324 ± 0.012 | 18 |
| 27.86 | 3.203 ± 0.011 | 22 |
| 28.79 | 3.101 ± 0.011 | 19 |
| 29.14 | 3.065 ± 0.010 | 18 |

In an embodiment, crystalline Form L is characterized by its powder XRD pattern which comprises peaks having a relative intensity of greater than or equal to about 25%, preferably peaks having a relative intensity of greater than or equal to about 40%.

In another embodiment, oxymorphone HCl, crystalline Form L is characterized by its pXRD pattern which comprises two or more of the form-specific peaks, as listed in Table L2, below. Where an overlapping Form listed in the Table below appears in parentheses, said Form exhibits peaks which may or may not overlap, depending on the resolution of the measured pXRD pattern.

TABLE L2

Form-specific pXRD peaks, Form L

| position °2θ | d-spacing (Å) | Overlaps w/Form |
|---|---|---|
| 9.58 ± 0.10 | 9.231 ± 0.097 | (D), F |
| 10.20 ± 0.10 | 8.669 ± 0.086 | A, H, J |
| 12.56 ± 0.10 | 7.050 ± 0.056 | C, J, K |

Crystalline Form M

Figure 11:
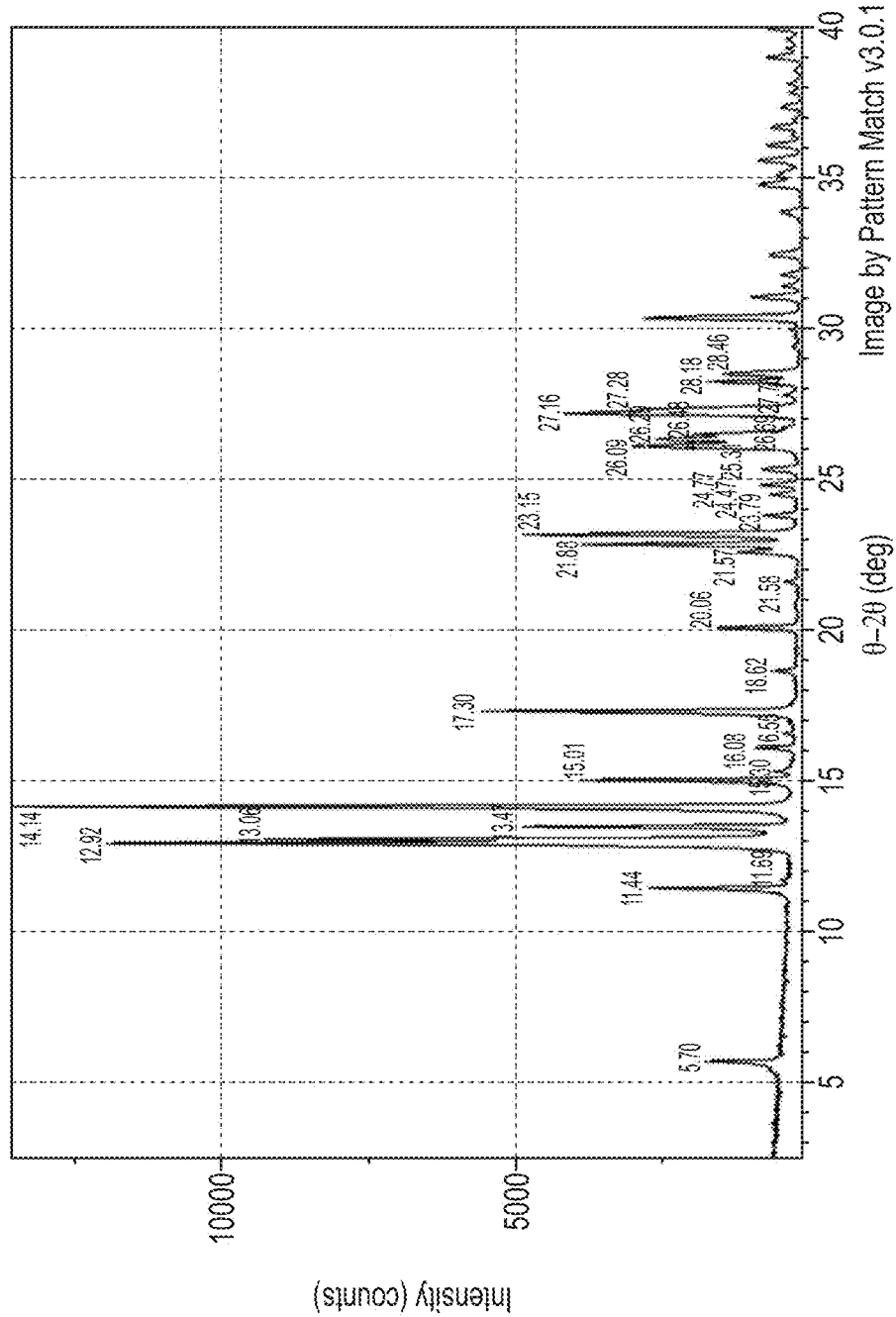
FIG. 11 illustrates a powder X-ray diffraction pattern of oxymorphone HCl crystalline Form M, expressed in terms of °2θ.

A representative sample of oxymorphone HCl crystalline Form M was analyzed using the PANalytic diffractometer as described above. Form M may be characterized by its pXRD peaks, as listed in Table M1, below. FIG. 11 illustrates a representative pXRD pattern for a representative sample of oxymorphone HCl crystalline form M.

TABLE M1 pXRD Observed Peaks, Oxymorphone HCl, Form M

| Position °2θ (±0.10) | d space (Å) | Relative Intensity (%) |
|---|---|---|
| 5.70 | 15.494 ± 0.276 | 13 |
| 11.44 | 7.738 ± 0.068 | 20 |
| 11.69 | 7.572 ± 0.065 | 4 |
| 12.92 | 6.850 ± 0.053 | 88 |
| 13.06 | 6.781 ± 0.052 | 68 |
| 13.47 | 6.571 ± 0.049 | 36 |
| 14.14 | 6.262 ± 0.044 | 100 |
| 15.01 | 5.902 ± 0.039 | 28 |
| 15.30 | 5.793 ± 0.038 | 4 |
| 16.08 | 5.511 ± 0.034 | 7 |
| 16.55 | 5.357 ± 0.032 | 3 |
| 17.30 | 5.125 ± 0.030 | 41 |
| 18.62 | 4.765 ± 0.025 | 5 |
| 20.06 | 4.427 ± 0.022 | 12 |
| 21.58 | 4.118 ± 0.019 | 3 |
| 22.57 | 3.940 ± 0.017 | 9 |
| 22.82 | 3.898 ± 0.017 | 28 |
| 23.15 | 3.842 ± 0.016 | 36 |
| 23.79 | 3.741 ± 0.016 | 6 |
| 24.47 | 3.638 ± 0.015 | 5 |
| 24.77 | 3.594 ± 0.014 | 6 |
| 25.31 | 3.519 ± 0.014 | 6 |
| 26.09 | 3.415 ± 0.013 | 22 |
| 26.29 | 3.390 ± 0.013 | 19 |
| 26.48 | 3.367 ± 0.013 | 15 |
| 26.69 | 3.340 ± 0.012 | 3 |

TABLE M1-continued pXRD Observed Peaks, Oxymorphone HCl, Form M

| Position °2θ (±0.10) | d space (Å) | Relative Intensity (%) |
|---|---|---|
| 27.16 | 3.283 ± 0.012 | 31 |
| 27.28 | 3.269 ± 0.012 | 22 |
| 27.76 | 3.213 ± 0.011 | 3 |
| 28.18 | 3.167 ± 0.011 | 13 |
| 28.46 | 3.136 ± 0.011 | 11 |

In an embodiment, crystalline Form M is characterized by its powder XRD pattern which comprises peaks having a relative intensity of greater than or equal to about 20%, preferably peaks having a relative intensity of greater than or equal to about 40%.

In another embodiment, oxymorphone HCl, crystalline Form M is characterized by its pXRD pattern which comprises two or more of the form-specific peaks, as listed in Table M2, below. Where an overlapping Form listed in the Table below appears in parentheses, said Form exhibits peaks which may or may not overlap, depending on the resolution of the measured pXRD pattern.

TABLE M2

Form-specific pXRD peaks, Form M

| position °2θ | d-spacing (Å) | Overlaps w/Form |
|---|---|---|
| 5.70 ± 0.10 | 15.494 ± 0.276 | J |
| 11.44 ± 0.10 | 7.738 ± 0.068 | A, B, C, H, L |
| 13.47 ± 0.10 | 6.571 ± 0.049 | F, G |

Single Crystal X-Ray Diffraction Analysis

Representative samples of the oxymorphone HCl crystalline forms A, B, H were also analyzed using single crystal X-ray diffraction analysis. Preliminary examination and data collection were performed with Mo $K_\alpha$ radiation ($\lambda$=0.71073 Å) on a Nonius KappaCCD diffractometer equipped with a graphite crystal, incident beam monochromator (Form A, Form B), or with Cu $K_\alpha$ radiation ($\lambda$=1.54184 Å) on a Rigaku Rapid II diffractometer equipped with confocal optics (Form H). Refinements were performed on an LINUX PC using SHELX97 [Sheldrick, G. M. *SHELX97, A Program for Crystal Structure Refinement*, University of Gottingen, Germany, 1997]. Cell constants and an orientation matrix for data collection were obtained from least-squares refinement. The refined mosaicity from DENZO/SCALEPACK [Otwinowski, Z.; Minor, W. *Methods Enzymol.* 1997, 276, 307] was used for the indication of good crystal quality. The space group was determined by the program XPREP [Bruker, XPREP in SHELXTL v. 6.12., Bruker AXS Inc., Madison, Wis., USA, 2002]. From the systematic presence of the following conditions: 0k0 k=2n etc., and from subsequent least-squares refinement, the space group was determined to be $P2_1$ (no. 4). The data were collected at a temperature of 150±1 K.

Single crystal X-ray diffraction analyses were completed for crystalline forms A, B and H, with the single crystals prepared as described in Examples 18, 19 and 20, respectively, which follow herein; and with results as presented in Table 2 below.

TABLE 2

Single Crystal Unit Cell Measurements

| Parameter symmetry space group | Form A monoclinic P2$_1$ (no. 4) | Form B monoclinic P2$_1$ (no. 4) | Form H monoclinic P2$_1$ (no. 4) |
|---|---|---|---|
| a (Å) | 10.9403(5) | 10.9177(5) | 14.2553(3) |
| b (Å) | 11.2063(3) | 15.2747(10) | 11.0185(2) |
| c (Å) | 14.2457(7) | 12.1873(8) | 33.4408(6) |
| α (°) | 90.00 | 90.00 | 90.00 |
| β (°) | 107.056(2) | 115.514(4) | 93.0352(9) |
| γ (°) | 90.00 | 90.00 | 90.00 |
| V (volume Å3) | 1669.72(12) | 1834.21(19) | 5242.25(17) |
| density (g/cm$_3$) | 1.443 | 1.339 | 1.430 |

Powder X-Ray Diffraction Pattern Indexing

The pXRD patterns for the oxymorphone HCl crystalline forms were subjected to indexing using Dicvol (Dicvol v6.0 Oct. 2006-D. Louer, A. Boultif). Indexing makes use of a peak list generated from measured powder X-ray diffraction patterns to calculate a crystal unit cell consistent with the peak list. As a result of indexing, each peak is associated with a Miller index (hkl) corresponding to the crystalline planes responsible for the peak. The ability to index a measured powder X-ray diffraction pattern and arrive at a unit cell whose volume is consistent with the molecular entity is consider to be proof that the measured pXRD data represents a single phase crystalline form. During the indexing, the initial long peak list is reduced to a smaller list of peaks that still indexes to the same unit cell. The symmetry, space group (S.G.) and lattice parameters (a, b, c, α, β, γ) for the unit cells derived for each of the single phase oxymorphone HCl crystalline forms is listed in Table 3 below. The unit cells expressed in Table 3 encompass by definition all symmetry related cells.

One skilled in the art will recognize that indexing of powder X-ray diffraction patterns is more approximate in the determination of unit cell parameters than single crystal X-ray diffraction, with a variability of at least ±0.1 Å in the lengths and ±0.5° in the angles of the unit cell. The quality of the indexing result is therefore strongly dependent on the quality of the measured pXRD pattern used as input.

TABLE 3

Single Crystal Parameter as Determined by pXRD Indexing

| Form | Symmetry | S.G. | a (Å) (±0.1) | b (Å) (±-0.1) | c (Å) (±0.1) | α (°) (±0.5) | β (°) (±0.5) | γ (°) (±0.5) |
|---|---|---|---|---|---|---|---|---|
| A | Monoclinic | P21 | 10.99 | 11.32 | 14.33 | 90 | 107.0 | 90 |
| B | Monoclinic | P21 | 10.76 | 15.18 | 12.18 | 90 | 115.9 | 90 |
| C | Orthorhombic | P212121 | 22.60 | 15.22 | 10.97 | 90 | 90 | 90 |
| D | Orthorhombic | P212121 | 23.45 | 15.05 | 11.15 | 90 | 90 | 90 |
| F | Orthorhombic | P212121 | 36.22 | 10.66 | 9.26 | 90 | 90 | 90 |
| G | Monoclinic | P21 | 7.45 | 17.99 | 14.25 | 90 | 104.32 | 90 |
| H | Monoclinic | P21 | 14.45 | 11.13 | 33.40 | 90 | 92.7 | 90 |
| J | Monoclinic | P21 | 17.19 | 5.445 | 32.13 | 90 | 94.019 | 90 |
| K | Orthorhombic | P212121 | 21.94 | 15.00 | 10.93 | 90 | 90 | 90 |
| L | Triclinic | P1 | 9.349 | 10.33 | 11.10 | 116.2 | 107.6 | 92.4 |
| M | Hexagonal | P61 | 7.9 | 7.9 | 46.37 | 90 | 90 | 120 |

For the most populous clusters, unit cell refinement was performed using Checkcell (CheckCell 2009, Jean Laugier, Bernard Bochu) and Unit_Cell (UnitCell 1997, T. J. B. Holland, S. A. T. Redfern "Unit cell refinement from powder diffraction data: the use of regression diagnostics". *Mineralogical Magazine* 61: 65-77). Unit cell refinement takes as input a limited number of peak positions and their Miller indices determined by indexing. Depending on the symmetry of the crystalline unit cell, only 3 or 4 observed peaks are required to calculate the complete crystalline unit cell using unit cell refinement.

In an embodiment, the present invention is directed to a crystalline form of oxymorphone HCl, wherein the pXRD pattern of Form B may be described by a monoclinic unit cell with parameters determined by powder X-ray diffraction indexing of a=10.76(10) Å, b=15.18(10) Å, c=12.18(10) Å and β=115.9(5)°;

wherein the pXRD pattern of Form C may be described by an orthorhombic unit cell with parameters determined by powder X-ray diffraction indexing to be a=22.60(10) Å, b=15.22(10) Å and c=10.97(50) Å;

wherein the pXRD pattern of Form D may be described by an orthorhombic unit cell with parameters determined by powder X-ray diffraction indexing to be a=23.45(10) Å, b=15.05(10) Å and c=11.15(10) Å;

wherein the pXRD pattern of Form F may be described by an orthorhombic unit cell with parameters determined by powder X-ray diffraction indexing to be a=36.22(10) Å, b=10.66(10) Å and c=9.26(10) Å;

wherein the pXRD pattern of Form G may be described by a monoclinic unit cell with parameters determined by powder X-ray diffraction indexing to be a=7.45(10) Å, b=17.99(10) Å, c=14.25(10) Å and β=104.35(50)°;

wherein the pXRD pattern of Form H may be described by a monoclinic unit cell with parameters determined by powder X-ray diffraction indexing to be a=14.45 Å, b=11.13 Å, c=33.40 Å and β=92.7°;

wherein the pXRD pattern of Form J may be described by a monoclinic unit cell with parameters determined by powder X-ray diffraction indexing to be a=17.19(10) Å, b=5.45(10) Å, c=32.13(20) Å and β=94.0(5)°;

wherein the pXRD pattern of Form L may be described by an orthorhombic unit cell with parameters determined by powder X-ray diffraction indexing to be a=9.35(10) Å, b=10.33(10) Å and c=11.10(10) Å;

and wherein the pXRD pattern of Form M may be described by an hexagonal unit cell with parameters determined by powder X-ray diffraction indexing to be a=7.90(10) Å, b=7.90(10) Å, c=46.37(20) Å and γ=120.0°.

Some of the crystalline forms of oxymorphone HCl as herein described were additionally analyzed by to one or more of the following techniques, with measurement and analysis conditions applied as listed below.

Differential Scanning Calorimetry (DSC)

Differential scanning calorimetry was performed using a TA Instruments differential scanning calorimeter 2920 or Q2000. The sample was placed into an aluminum DSC pan, and the weight accurately recorded. The pan was covered with a lid pierced with a laser pinhole and then hermetically sealed (HSLP or T0HSLP). Alternately, the sample was covered with a lid and crimped (C). Reported temperatures are peak maxima, unless otherwise specified.

Differential scanning calorimetry (DSC) was performed on representative samples of oxymorphone HCl Form A, Form B, Form D, Form J and Form M, as shown in FIG. 12, FIG. 15, FIG. 20, FIG. 21 and FIG. 22, respectively.

Thermogravimetric Analysis (TGA)

Thermogravimetric analyses were performed using a TA Instruments 2950 thermogravimetric analyzer. Each sample was placed in an aluminum sample pan and inserted into the TG furnace. The furnace was started directly from ambient temperature, then heated under nitrogen at a rate of 10° C./min, up to a final temperature of 350° C. Nickel and Alumel™ were used as the calibration standards.

Figure 12:
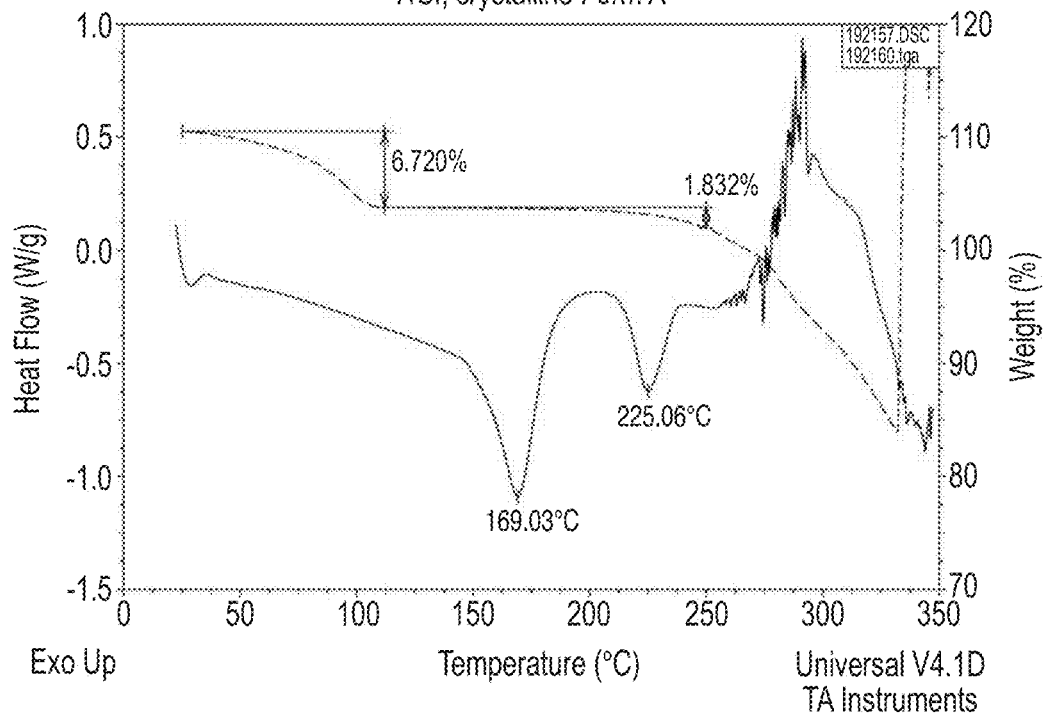
FIG. 12 illustrates a measured DSC (solid line) and TGA (broken line) profiles for oxymorphone HCl crystalline Form A.
Figure 15:
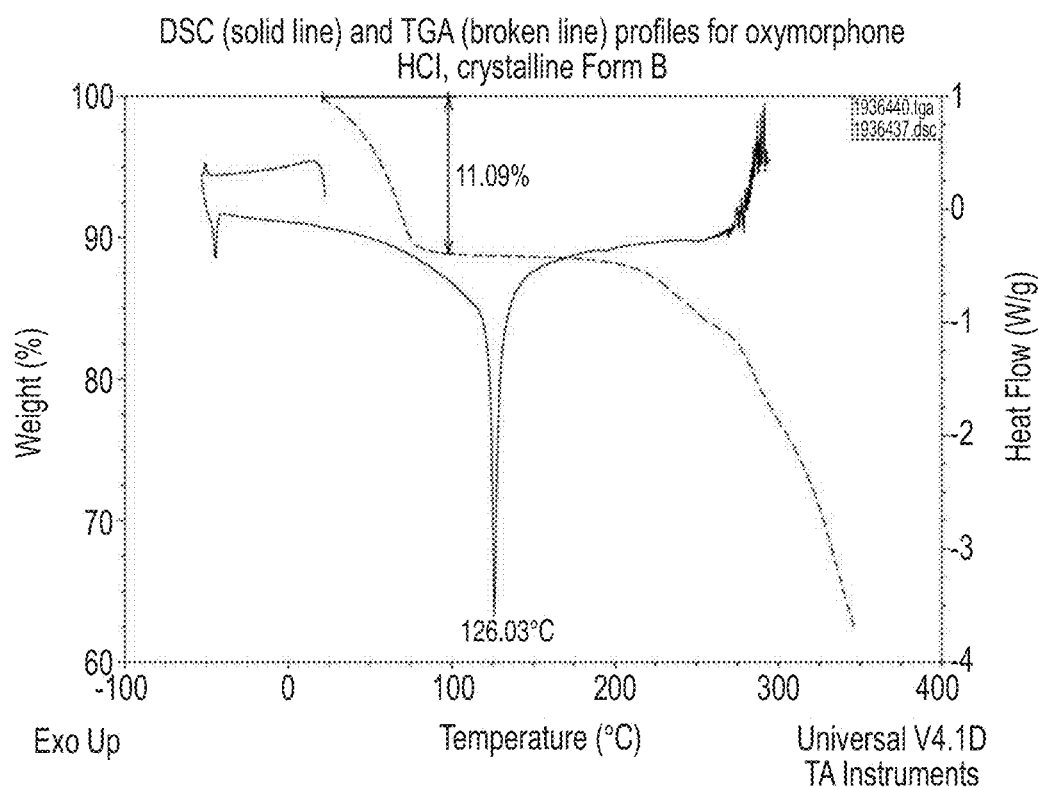
FIG. 15 illustrates a measured DSC (solid line) and TGA (broken line) profiles for oxymorphone HCl crystalline Form B.
Figure 18:
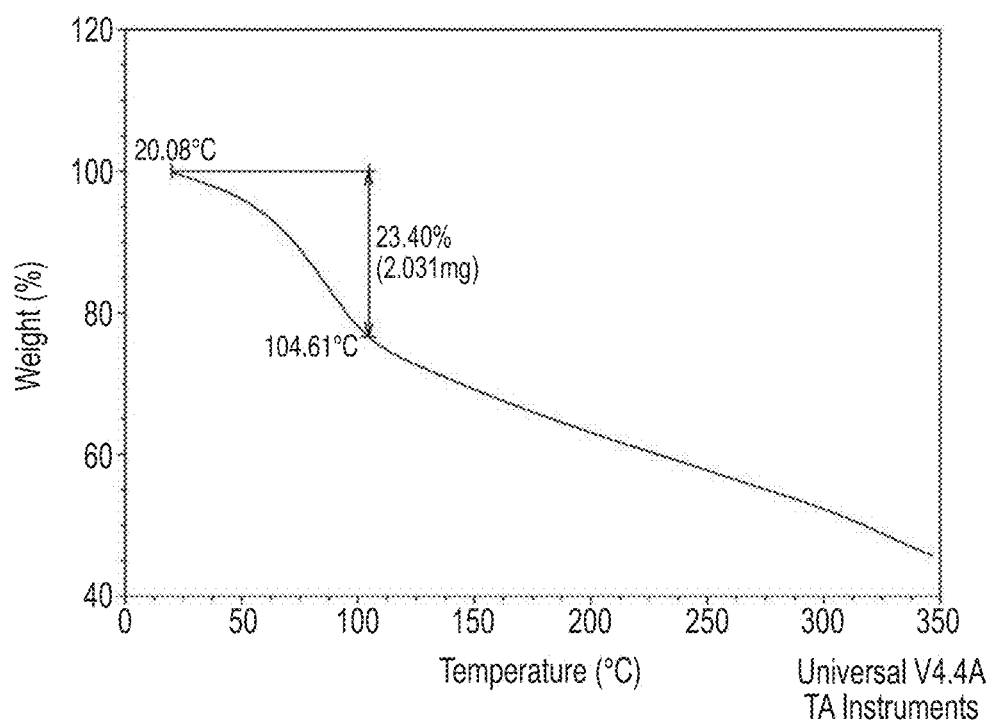
FIG. 18 illustrates a measured TGA profile for oxymorphone HCl crystalline Form C.
Figure 20:
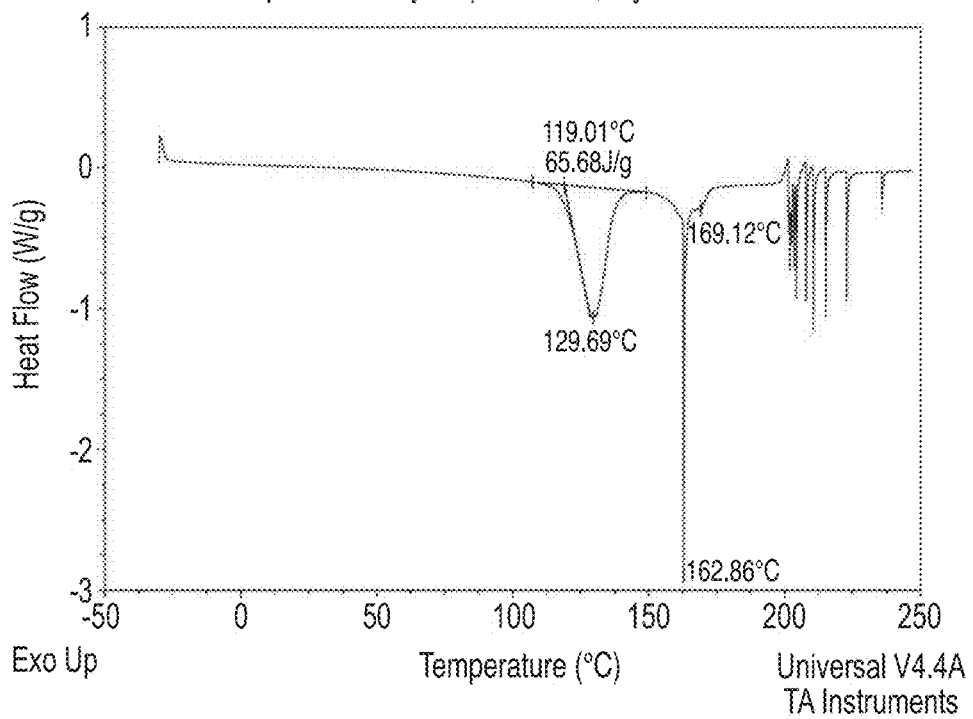
FIG. 20 illustrates a measured DSC profile for oxymorphone HCl crystalline Form D.
Figure 21:
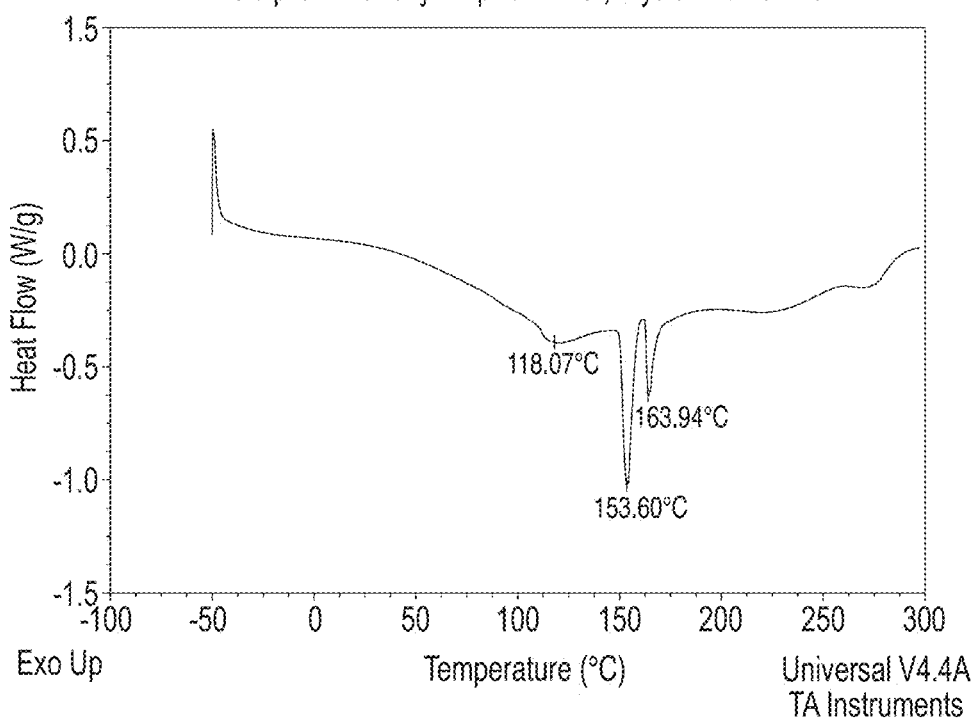
FIG. 21 illustrates a measured DSC profile for oxymorphone HCl crystalline Form J.
Figure 22:
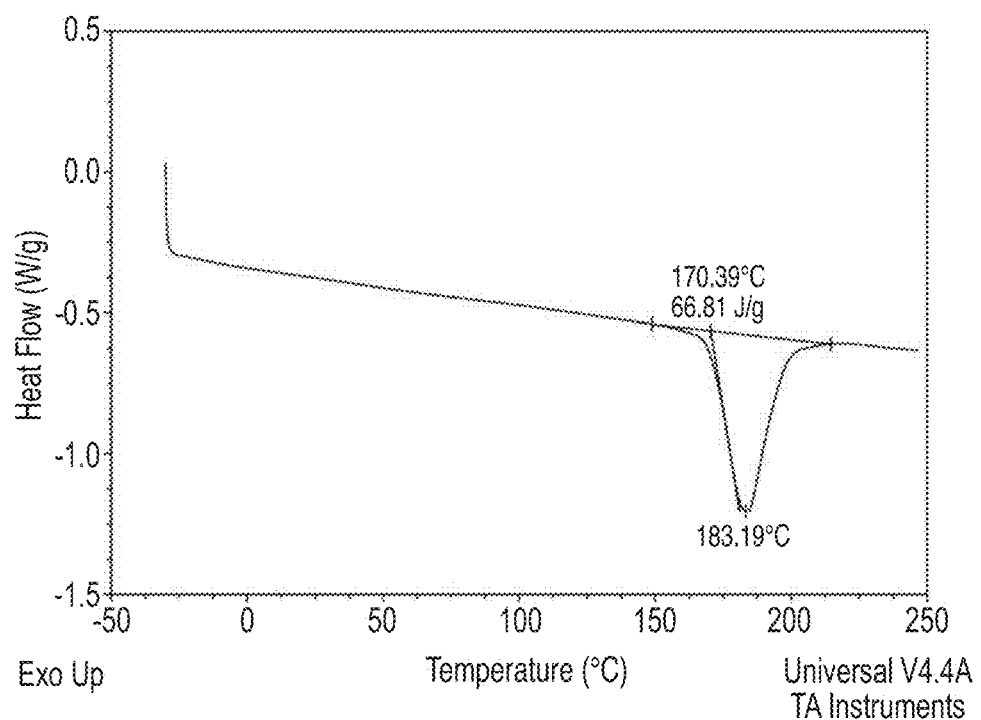
FIG. 22 illustrates a measured DSC profile for oxymorphone HCl crystalline Form M.
Figure 23B:
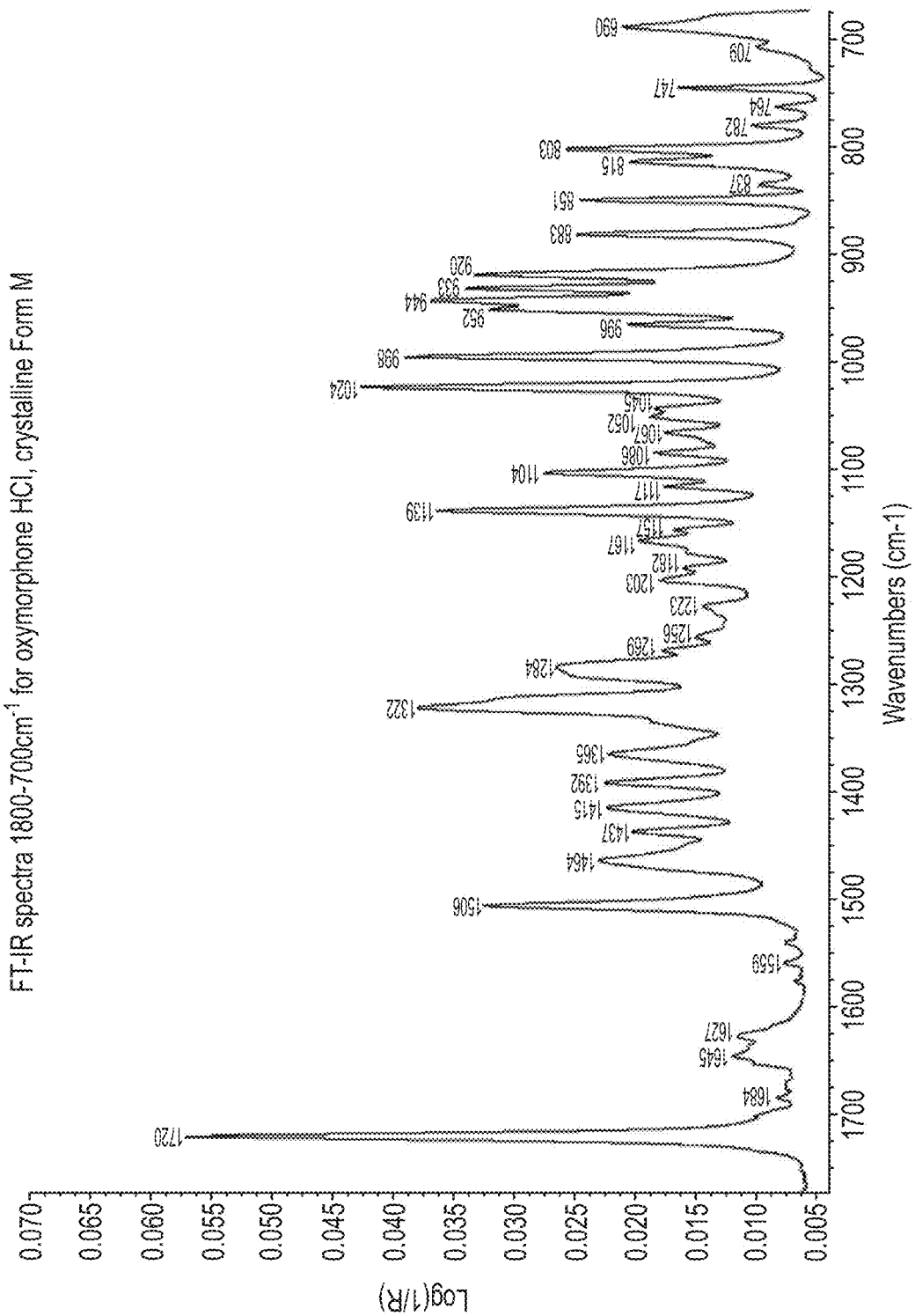
FIG. 23, parts A and B, illustrate an FT-IR spectra for oxymorphone HCl crystalline Form M.

Thermogravimetric analysis (TGA) was performed on representative samples of oxymorphone HCl Form A, Form B and Form C, as shown in FIG. 12, FIG. 15 and FIG. 18, respectively.

Karl-Fischer Titration

Coulometric Karl Fischer (KF) analysis for water determination was performed using a Mettler Toledo DL39 Karl Fischer titrator. A weighed amount of sample was placed in the KF titration vessel containing Hydranal—Coulomat AD and mixed to ensure dissolution. The sample was then titrated by means of a generator electrode which produces iodine by electrochemical oxidation: $2\ I-\geq I_2+2e$. When sample size was sufficient, replicates were obtained to ensure reproducibility.

Karl-Fischer analysis was performed on representative samples of oxymorphone HCl Form A, Form D, Form J and Form M, with results as provided herein.

Dynamic Vapor Moisture Sorption/Desorption Analysis

Dynamic vapor sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Figure 13:
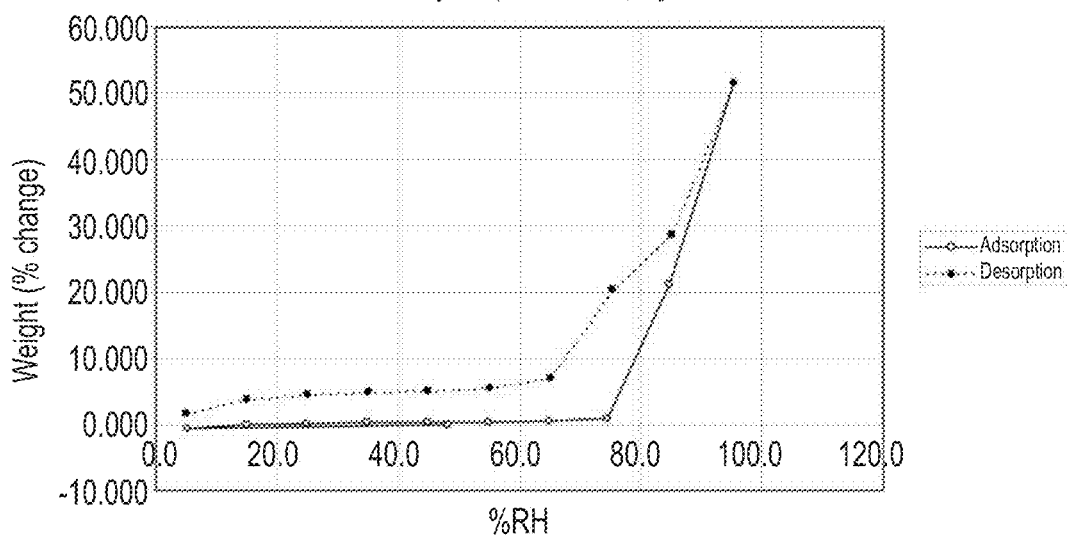
FIG. 13 illustrates an automated sorption (open circle)/desorption (filled circle) profile measured for oxymorphone HCl crystalline Form A.
Figure 16:
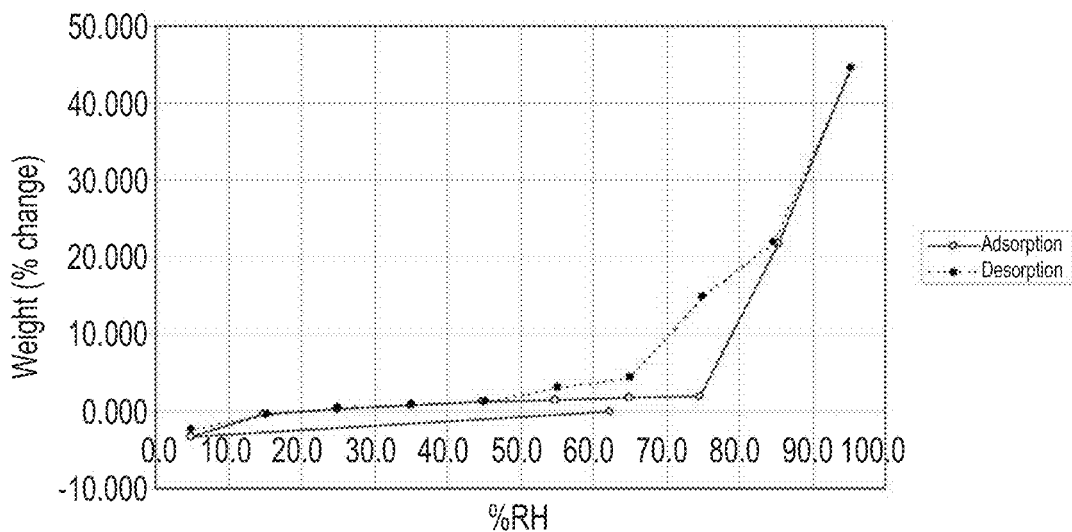
FIG. 16 illustrates an automated sorption (open circle)/desorption (filled circle) profile measured for oxymorphone HCl crystalline Form B.
Figure 17A:
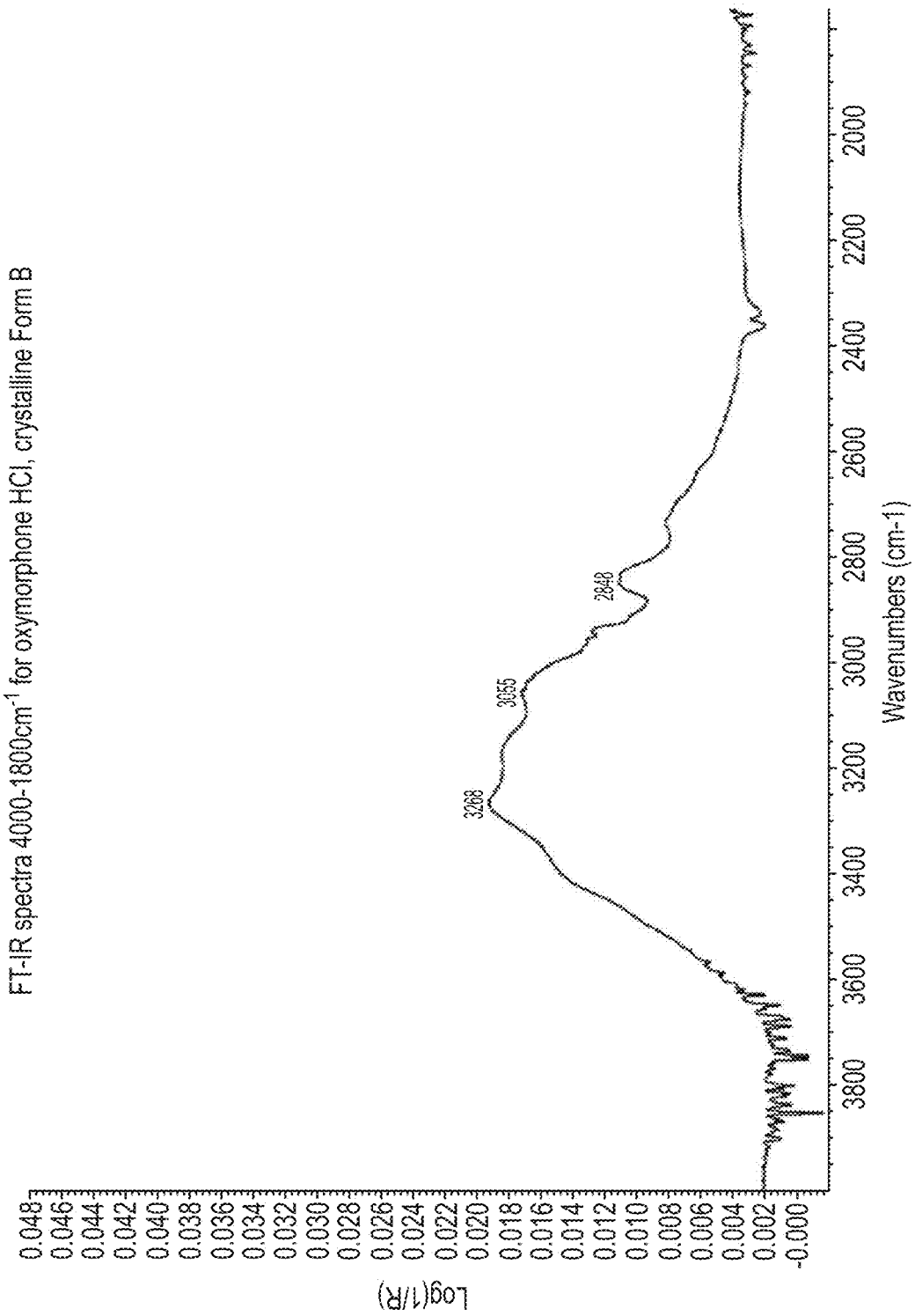
FIG. 17, parts A and B, illustrate an FT-IR spectra for oxymorphone HCl crystalline Form B.

Dynamic vapor moisture sorption/desorption data was collected for representative samples for oxymorphone HCl Form A and Form B, as shown in FIG. 13 and FIG. 16, respectively.

Fourier Transform Infrared Spectroscopy (FT-IR)

Infrared (IR) spectra were acquired for a representative sample of oxymorphone HCl, Form A on Magna-IR 860® Fourier transform infrared (FT-IR) spectrophotometer (Thermo Nicolet) equipped with an Ever-Glo mid/far IR source and a deuterated triglycine sulfate (DTGS) detector. An attenuated total reflectance (ATR) accessory (Thunderdome™, Thermo Spectra-Tech), with a germanium (Ge) crystal was used for data acquisition. Each spectrum represents 256 co-added scans collected at a spectral resolution of 4 $cm^{-1}$. A background data set was acquired with a clean Ge crystal. Log 1/R(R=reflectance) spectra were acquired by taking a ratio of these two data sets against each other. Wavelength calibration was performed using polystyrene.

A Continuμm™ infrared microscope (Thermo Spectra-Tech) with a mercury cadmium telluride (MCT) detector interfaced to a Magna-IR 560® Fourier transform infrared (FT-IR) spectrophotometer (Thermo Nicolet) was used to analyze representative samples of oxymorphone HCL crystalline forms B, C and M. The microscope was operated in the reflection mode for all analyses. The attenuated total reflectance (ATR) spectra were obtained with an ATR objective containing a Ge internal reflection element (IRE). The spectra were collected in the ATR mode. The background spectra for the ATR analyses were collected with the ATR objective in the non-contacting mode. A total of 256 sample scans were collected from 4000-675 $cm^{-1}$ at a spectral resolution of 4 $cm^{-1}$, using Happ-Genzel apodization. Wavelength calibration was performed using polystyrene Fourier transform infrared spectra were collected for representative samples of oxymorphone Form A, Form B, Form C and Form M, as shown in FIG. 14, FIG. 17, FIG. 19 and FIG. 23, respectively.

Proton Nuclear Magnetic Resonance ($^1$H NMR)

The 1HNMR spectra were collected for representative samples of oxymorphone HCl Form D and Form M. For measurement, samples were prepared for proton nuclear magnetic resonance ($^1$H-NMR) spectroscopy as ~5-50 mg solutions in DMSO-$d_6$.

Optical Microscopy

Optical microscopy was performed using a Leica MZ12.5 stereomicroscope. Various objectives typically ranging from 0.8-10× were used with crossed-polarized light to view samples. Samples were viewed in situ. Where a particular crystalline Form was prepared under different crystallization conditions, said crystallization conditions may have resulted in different crystalline morphology, as noted in more detail herein.

Crystalline Form Summaries

The following are summaries of the physical properties of oxymorphone HCl crystalline Forms A, B, C, D, F, G, H, J, K, L and M, based on the measurements and analyses completed as described herein.

Oxymorphone HCl Crystalline Form A

Oxymorphone HCl crystalline Form A is the commercially produced form. Crystalline Form A is a sesquihydrate, as confirmed by single crystal x-ray diffraction structure analysis. The monoclinic cell parameters and calculated volume are: a=10.9403(5), b=11.2063(3), c=14.2457(7) Å, α=90.00, β=107.056(2), γ=90.00°, V=1669.72(12) Å$^3$. The formula weight of the asymmetric unit in the crystal structure of oxymorphone hydrochloride is 362.81 g/mol with Z=4, resulting in a calculated density of 1.443 g $cm^{-3}$. The space group was determined to be P2$_1$ (no. 4).

A sesquihydrate contains 1.5 moles of water per mole of the molecule in the crystalline unit cell. The Karl Fisher (KF) water titration data for crystalline Form A showed about 7.5% of water. This corresponds to 1.5 moles of water per mole of oxymorphone HCl, consistent with the determination that this form is a sesquihydrate. Upon heating, crystals of Form A lost the water molecules and melting beginning at about 218° C., with melt completing at about 237° C. TGA (thermogravimetric analysis) data showed a weight loss of 6.5% between 25° C. and 112° C., equating to approximately 1.5 mole of water. DSC (differential scanning calorimetry) data showed a broad endotherm near 165° C. corresponding to the water loss, followed by an endotherm near 230° C., corresponding to the melting. Form A exhibited hygroscopicity at relative humidity (RH) above 75% in dynamic vapor sorption/desorption analysis. Moisture uptake of about 50% by weight was observed between 75% and 95% RH. During the desorption cycle, hysteresis was observed and the sample retained 2.4% of moisture at the end of the cycle (at 5% RH).

The infrared (FT-IR) spectrum of a representative sample of crystalline Form A exhibited unique peaks when compared with the FT-IR spectra of crystalline Form B, Form C and Form M.

Depending on crystallization conditions, Form A was isolated as needles, tablets or as a form of indeterminate morphology.

Oxymorphone HCl Crystalline Form B

Oxymorphone HCl Form B is a dihydrate confirmed by single crystal x-ray diffraction structure analysis. The monoclinic cell parameters and calculated volume are: a=10.9177(5) Å, b=15.2747(10) Å, c=12.1873(8) Å, α=90.00°, β=115.514(4)°, γ=90.00°, V=1834.21(19) Å$^3$. The formula weight of the asymmetric unit in the crystal structure of oxymorphone hydrochloride Form B was 369.81 g/mol with Z=4, resulting in a calculated density of 1.339 g cm$^{-3}$. The space group was determined to be P2$_1$ (no. 4). The single crystal X-ray diffraction study was performed at low temperature (150K). The monoclinic unit cell derived by indexing is: a=10.76(10) Å, b=15.18(10) Å, c=12.18(10) Å and β=115.9(5)°.

The determination that crystalline Form B is a dihydrate was consistent with TGA data, which showed 11% of weight loss, which corresponds to about 2 moles of water per mole of oxymorphone HCl. DSC data showed a single endotherm at 126° C. Crystalline Form B exhibited hygroscopicity above 75% RH (relative humidity) in dynamic vapor sorption/desorption analysis. Moisture uptake of about 43% by weight was observed between 75% and 95% RH. During the desorption cycle, no hysteresis was observed between 45% RH and 5% RH, and the sample returned to the initial moisture content at the end of the cycle.

The FT-IR spectrum of a representative sample of crystalline Form B exhibited unique peaks when compared with crystalline Form A, Form C and Form M samples, indicating that IR spectroscopy can be used to characterize Form B samples.

Crystalline Form B was physically stable under mechanical grinding studies in the presence of a small quantity of water. However, Form B was partially converted to Form A when the crystalline sample was mechanically ground in the absence of water.

Crystalline sample of Form B was prepared from evaporation crystallizations from acetone/water (15:1 v:v), either via fast evaporation (evaporation of solvent from an open vial) or via slow evaporation (evaporation of solvent from a vial covered with aluminum foil with one or more pin holes). Crystalline Form B was also crystallized from a solution of oxymorphone HCl in ethyl acetate and water via ultrasonication precipitation or from fast evaporation of trichloroethanol/methanol (32:5 v:v).

Depending on crystallization conditions, Form B was isolated as dendritic, blades, fine needles, plates, flakes, white particulates and as a form of indeterminate morphology.

Oxymorphone HCl Crystalline Form C

Oxymorphone HCl crystalline Form C is a unique crystalline phase confirmed by indexing the pXRD data, having orthorhombic P212121 structure with unit cell parameters of 22.60(10) Å, 15.22(10) Å, 10.97(10) Å (length of a, b, c, respectively). Based on the unit cell volume, the crystalline form appears to be a solvate. This is consistent with TGA data which showed about 23% of weight less from ambient to about 105° C. Even though the solvent was lost below 100° C. in the TGA, the crystalline Form C was stable at ambient temperature storage when re-analyzed after approximately 12 months.

The FT-IR spectrum of a representative sample of crystalline Form C exhibited unique peaks when compared to with Form A, Form B and Form M samples, indicating that IR spectroscopy can be used to characterize Form C samples.

Crystalline Form C samples were obtained as needles in two different ways: (1) fast evaporation of solutions from chloroform:tetrahydrofuran:methanol (35:10:1, v:v), or tetrahydrofuran:water (50:3, v:v), and (2) slow evaporation from tetrahydrofuran:methanol (10:3, v:v).

Depending on crystallization conditions, Form C was isolated as small fine needles, dendritic needles and as a form of indeterminate morphology.

Oxymorphone HCl Crystalline Form D

Oxymorphone HCl crystalline Form D is a unique crystalline phase confirmed by indexing the pXRD data, having orthorhombic P212121 structure with unit cell parameters of 23.45 Å, 15.05 Å, 11.15 Å (length of a, b, c, respectively). Karl-Fisher water analysis showed only 1 mole of water even though the unit cell volume indicated larger volume of water can be present. Proton NMR spectrum of a representative sample did not show any organic solvent, indicating that the sample is a hydrate. DSC data exhibited an event corresponding to the water loss near 130° C., then possible melting event near 163° C.

Crystalline Form D sample was unstable at ambient temperature storage when re-analyzed after approximately 12 months, converting to a mixture of Form A and Form B, both of which are hydrates. Crystalline Form D samples were obtained as small rods consistently from fast evaporation of solutions from hexafluoroisopropanol.

Depending on crystallization conditions, Form D was isolated as dendrites and small rods.

Oxymorphone HCl Crystalline Form F

Oxymorphone HCl crystalline Form F is a unique crystalline phase confirmed by indexing the pXRD data, having orthorhombic P212121 structure with unit cell parameters of 36.22 Å, 10.66 Å, 9.26 Å (length of a, b, c, respectively). The unit cell volume indicated water may be present.

Crystalline Form F sample was unstable at ambient temperature storage, converting to Form A which is a hydrate after approximately 10 months. Crystalline Form F samples were precipitated from a solution of methanol by adding an anti-solvent such as dichloromethane or methyl ethyl ketone.

Depending on crystallization conditions, Form F was isolated as blades and flakes.

Oxymorphone HCl Crystalline Form G

Oxymorphone HCl crystalline Form G is a unique crystalline phase confirmed by indexing the pXRD data, having monoclinic P21 structure with unit cell parameters of 7.45 Å, 17.99 Å, 14.25 Å (length of a, b, c, respectively) and β angle of 104.32°. The unit cell volume indicated water may be present.

Crystalline Form G was unstable at ambient temperature storage, converting to Form A, which is a hydrate, after approximately 10 months. Crystalline Form G was obtained as white needles from slurry of oxymorphone HCl (Form B) in isopropanol (IPA) at 60° C. for two days. However, when the slurry experiment was carried out at ambient temperature for 6 days, a mixture of Form A and Form G was obtained.

Form G was isolated as needles.

Oxymorphone HCl Crystalline Form H

Oxymorphone HCl crystalline Form H is a monohydrate and hemi-acetonitrile solvate confirmed by single crystal x-ray diffraction structure analysis. The monoclinic cell parameters and calculated volume are: a=14.2553(3) Å, b=11.0185(2) Å, c=33.4408(6) Å, a=90°, β=93.0352(9)°, γ=90°, V=5245.25(17) Å$^3$. The formula weight of the asymmetric unit in the crystal structure of oxymorphone HCl Form H is 376.35 g/mol with Z=12, resulting in a calculated density of 1.430 g cm$^{-3}$. The space group was determined to be P2$_1$ (no. 4). The single crystal X-ray diffraction study was performed at low temperature (150K). The monoclinic unit cell derived by indexing is: a=14.45(10) Å, b=11.13 (10) Å, c=33.40(20) Å and β=92.7(5)°.

Crystalline Form H was prepared by exposing a solution of oxymorphone HCl Form B in acetonitrile water (20:0.1, v:v) to a vapor of acetonitrile. Crystalline Form H was also obtained when a solid sample of oxymorphone HCl (Form B) was exposed to acetonitrile vapor for about 2.5 weeks at ambient temperature. Crystalline Form H sample was unstable at ambient temperature storage, converting to Form A, which is a hydrate, after approximately 10 months.

Depending on crystallization conditions, Form H was isolated as plates and fine particulates.

Oxymorphone HCl Crystalline Form J

Oxymorphone HCl crystalline Form J is a unique crystalline phase confirmed by indexing the pXRD data, having monoclinic P21 structure with unit cell parameters of 17.19 Å, 5.45 Å, 32.13 Å (length of a, b, c, respectively) and β angle of 94.02°. The unit cell volume indicated water and/or solvent may be present. Crystalline Form J is a mixed solvate of water-methyl ethyl ketone, containing about one mole of each. This was confirmed by Karl Fisher water analysis and proton NMR spectroscopy. DSC data showed multiple events near 118° C., 154° C. and 164° C., which are unique and different from other crystalline forms of oxymorphone HCl.

Crystalline Form J sample was obtained when a solid sample of oxymorphone HCl (a crystalline mixture containing mostly Form B) was exposed to methyl ethyl ketone vapor for over two weeks at ambient temperature. Longer term exposure of crystalline Form J, over five weeks, resulted in a mixture of Form J and Form A.

Form J was isolated as particles.

Oxymorphone HCl Crystalline Form K

Oxymorphone HCl Form K is a unique crystalline phase confirmed by indexing the pXRD data, having orthorhombic P212121 structure with unit cell parameters of 21.94 Å, 15.00 Å, 10.93 Å (length of a, b, c, respectively). The unit cell volume indicated water or solvent may be present.

Crystalline Form K sample was precipitated into plates and needles from a solution of acetonitrile:water (15:1, v:v) by rapidly cooling in an ice/water bath, followed by cooling in a refrigerator (approximately 5° C.) for 7 days.

Form K was isolated as plates.

Oxymorphone HCl Crystalline Form L

Oxymorphone HCl Form L is a unique crystalline phase confirmed by indexing the pXRD data, having triclinic P1 structure with unit cell parameters of 9.35 Å, 10.33 Å, 11.10 Å (length of a, b, c, respectively) and 116.2°, 107.6°, 92.4° (angles of α, β, γ, respectively). The unit cell volume indicated water or solvent may be present. The proton NMR spectrum of a representative sample of crystalline Form L confirmed the presence of 0.5 mole of ethanol per mole of oxymorphone HCl.

Crystalline Form L sample was precipitated from a saturated solution in ethanol at 60° C. by rapidly cooling to ambient temperature. Crystalline Form L was unstable at ambient temperature storage, converting to a mixture of crystalline forms, one of which is Form A (a sesquihydrate) and the other is a monohydrate/hemi-ethanolate after approximately 10 weeks. This suggests oxymorphone HCl crystalline Form L sample is a mixed solvate containing both water and ethanol.

Oxymorphone HCl Crystalline Form M

Oxymorphone HCl crystalline Form M is a unique crystalline phase confirmed by indexing the pXRD data, having a hexagonal P61 structure with unit cell parameters of 7.9 Å, 7.9 Å, 46.37 Å (length of a, b, c, respectively). The unit cell volume indicated water or solvent may be present. Karl Fisher water analysis showed only trace amounts of water. Proton NMR spectrum showed about half mole of ethanol per mole of oxymorphone HCl. This suggests that oxymorphone HCl crystalline Form M is an ethanol solvate. DSC analysis of the sample showed a sharp melt at 183° C. (peak maximum) which is unique and different from other crystalline forms of oxymorphone HCl.

The FT-IR spectrum of a representative sample of crystalline Form M exhibited unique peaks when compared with Form A, Form B and Form C samples, indicating that IR spectroscopy can be used to characterize Form M samples.

Crystalline Form M sample was obtained from a slurry of oxymorphone HCl (Form A) in ethanol at 60° C. for three days. However, when the slurry experiment was carried out for two days, the resulting product was a mixture of crystalline forms A, C and M, whereas the slurry experiment performed at ambient temperature for 10 days yielded a mixture of crystalline Form B and Form C.

Pharmaceutical Compositions

The present invention also provides pharmaceutical compositions comprising one or more of the oxymorphone HCl crystalline forms as herein described in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of providing an analgesic effect described in the present invention may also be carried out using a pharmaceutical composition comprising any of the compounds as defined herein and a pharmaceutically acceptable carrier. The pharmaceutical composition may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

The oxymorphone HCl crystalline forms as herein described may be administered in any of the foregoing compositions and according to dosage regimens established in the art whenever analgesia is required.

The daily dosage of the products may be varied over a wide range from 0.01 mg to about 1,000 mg per adult human per day, or any amount or range therein, preferably from about 5 mg to about 50 mg per adult human per day, or any amount or range therein. For oral administration, the compositions are preferably provided in the form of tablets containing about, 0.01, 0.05, 0.1, 0.5, 1.0, 2.5, 5.0, 7.5, 10, 25, 50, 100, 150, 250, 300, 400, 500 and 1000 milligrams of the active ingredient for the symptomatic adjustment of the dosage to the patient to be treated. An effective amount of the drug is ordinarily supplied at a dosage level of from about 0.01 mg/kg to about 15 mg/kg of body weight per day, or any amount range therein. Preferably, the range is from about 0.05 to about 10 mg/kg of body weight per day, or any amount or range therein. Preferably, the range is from about 0.1 to about 7 mg/kg of body weight per day, or any amount or range therein. Preferably, the range is from about 1 to about 5 mg/kg of body weight per day, or any amount or range therein. The compounds may be administered on a regimen of 1 to 4 times per day.

Optimal dosages and dosage regimens to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Preparation of Form A

Oxymorphone HCl (58.9 mg, Form B) was combined with chloroform (400 μL) with sonication. Solids remained and the vial was capped, sealed with PARAFILM and placed on a 60° C. shaker block. After 2 days of shaking at 60° C., no solvent remained and dry white solids were obtained. The solids were determined to be oxymorphone HCl, Form A.

Example 2

Preparation of Form A

Oxymorphone HCl (67.7 mg, Form B) was combined with ethyl acetate (400 μL) with sonication and shaking. Solids remained and the vial was capped, sealed with PARAFILM and placed on a 60° C. shaker block. After 2 days of shaking at 60° C., white solids were recovered by vacuum filtration and allowed to air-dry. White solids were obtained after 4 days of air-drying. The solids were determined to be oxymorphone HCl, Form A.

Example 3

Preparation of Form A

Oxymorphone HCl (33.7 mg, Form B) was combined with methyl ethyl ketone (500 μL). The vial was capped, sealed with PARAFILM and placed on a rotating wheel. After 10 days of mixing at ambient temperature on the rotating wheel, solids were present and the vial was removed from the rotating wheel and placed on the lab bench overnight. Solids were recovered by vacuum filtration and allowed to air-dry for 3 days after which time very small, white needles exhibiting birefringence and extinction were obtained. The white needle solids were determined to be oxymorphone HCl, Form A.

Example 4

Preparation of Form B

Oxymorphone free base (5.0027 g) was combined with water (2.5 mL) and 2-propanol (6.0 mL) in a round bottom flask (250 mL). The resulting mixture was heated in a temperature controlled bath, with stirring, from ambient to 60° C. over a time period of approximately 30 minutes. Concentrated hydrochloric acid (1.8 mL) was added with continued stirring. The temperature was increased to 70° C. resulting in a clear solution and then cooled to 60° C. 2-propanol was added in 3-5 mL aliquots over approximately 5 minute time span. Solids were observed after the addition of the second aliquot. The resulting slurry was cooled from 60 to 5° C. over 190 minutes and stirred at 5° C. for 45 minutes. Tan solids in a brown solution were observed. The flask was removed from the bath, the contents were vacuum filtered and the solids rinsed 5 times with 1 mL aliquots of 2-propanol:water (9:1 v:v). The resulting white solids were allowed to air-dry for 2 days to yield Form B oxymorphone HCl.

Example 5

Preparation of Form B

Oxymorphone HCl (65.9 mg, Form B) was combined with toluene (500 μL). The vial was capped, sealed with PARAFILM and placed on a rotating wheel. After 10 days at ambient conditions, solids were recovered by vacuum filtration and allowed to air-dry for 3 days to yield Form B oxymorphone HCl.

Example 6

Preparation of Form B

Oxymorphone HCl (43.8 mg, Form B) was dissolved in methanol (500 μL) and water (200 μL) with sonication and shaking. The resultant clear solution was filtered (0.2 μm) into a clean vial and the vial covered with aluminum foil pierced with pinholes. Solvent was allowed to evaporate under ambient conditions (allowed to evaporate for about four weeks) to yield very fine while needles exhibiting birefringence and extinction. The white needle solids were determined to be oxymorphone HCl, Form B.

Example 7

Preparation of Form B

Oxymorphone HCl (35.3 mg, Form B) was combined with acetone (15 mL) with sonication and shaking resulting in a cloudy solution. A clear solution was observed after the addition of water (1 mL). The solution was filtered (0.2 μm filter) into a clean vial and the vial covered with aluminum foil pierced with 3 pinholes. Solvent was allowed to evaporate for 3 weeks under ambient conditions to yield white dendritic solids exhibiting birefringence and extinction. The white dendritic solids were determined to be oxymorphone HCl, Form B.

Example 8

Preparation of Form C

Oxymorphone HCl (25.5 mg, Form B) was dissolved in chloroform (35 mL), tetrahydrofuran (10 mL) and methanol (1 mL) with sonication and shaking. The resultant clear solution was filtered (0.2 µm filter) into a clean vial and left uncapped. Solvent was allowed to evaporate for about one week under ambient conditions to yield white dendritic needles exhibiting birefringence and extinction. The solids were analyzed by pXRD as Form C and stored in ambient conditions. Re-analysis by pXRD after storage in ambient conditions was performed. The solids were determined to remain Form C.

Example 9

Preparation of Form D

Oxymorphone HCl (26.6 mg, Form B) was dissolved in 1,1,1,3,3,3-hexafluoroisopropanol (HFIPA, 100 µL) resulting in a clear solution. Cloudiness was observed after additional HFIPA (1000 µL) was added. The solution was filtered (0.2 µm) into a clean vial and solvent allowed to evaporate under ambient conditions for one week to yield white dendritic solids exhibiting birefringence and extinction. The white dendritic solids were determined to be oxymorphone HCl, Form D.

Example 10

Preparation of Form D

Oxymorphone HCl (199.2 mg, Form A) was dissolved in HFIPA (5 mL) with sonication resulting in a clear solution. The vial was capped and allowed to sit for one day. The solution was then filtered into a clean vial and solvent allowed to evaporate under ambient conditions. After about one week, solids exhibiting birefringence and extinction were obtained. The solids were determined to be oxymorphone HCl, Form D.

Example 11

Preparation of Form F

Oxymorphone HCl (67.3 mg, Form B) was dissolved in methanol (1 mL). The resultant clear solution was filtered (0.2 µm filter) into dichloromethane (500 µL) that had been pre-chilled in an ice/water bath. The slightly cloudy solution was placed in the freezer. After about 3 months, solids were recovered by vacuum filtration and allowed to air-dry to yield white blades and flakes exhibiting birefringence and extinction. The white blade and flake dendritic solids were determined to be oxymorphone HCl, Form D.

Example 12

Preparation of Form G

Oxymorphone HCl (40.2 mg, Form B) was weighed into a vial. Isopropyl alcohol (IPA, 2 mL) and magnetic stir bar were added and the mixture was stirred on a hot plate set at 60° C. and 300 rpm for 2 days. Solids were recovered by vacuum filtration and air-dried in the fume hood to yield white needles. The white needles were determined to be oxymorphone HCl, Form G.

Example 13

Preparation of Form H

Oxymorphone HCl (26.8 mg, Form B) was weighed into a one-dram vial. The vial was then placed open inside a 20-mL size scintillation vial containing acetonitrile (2 mL) and the scintillation vial capped. Solids were exposed to the solvent vapor for 17 days to yield fine white particles. The white particles were determined to be oxymorphone HCl, Form H.

Example 14

Preparation of Form J

Oxymorphone HCl (1.4541 g, Form A) was combined with tert-butanol (50 mL) in a round bottom flask (125 mL) with sonication. Solids remained. Hydrochloric acid (5.144 mL of 0.985N in water) was added. Water (5.0 mL) was added, and after sonication, the slightly cloudy solution was filtered (5.0 µm filter) into a clean flask. The solution was frozen in a bath of liquid nitrogen and placed in a lyophilizer jar prior to placing on to a freeze dryer. After 3 days, the flask was removed from the freeze dryer and observed to yield a solid sample exhibiting a mixture of crystalline forms. A portion of this sample (236.7 mg) was placed in a Petri dish (6 cm diameter, 1 cm height). The dish was placed in a jar containing sufficient methyl ethyl ketone to cover the bottom of the jar. The jar was sealed and stored in the dark at ambient temperature. After 1 day, the solids were mixed with a spatula and returned to the jar. After an additional 15 days, the solid were isolated and determined to exhibit the pXRD pattern of Form J.

Example 15

Preparation of Form K

Oxymorphone HCl (26.4 mg, Form B) was placed in a 1-dram vial. Acetonitrile/water (15/1 v/v, 2 mL) was added and the solution stirred on a hot plate set at 60° C. After approximately 4 hours, a very small quantity of solids remained. The solution was filtered (0.2 µm filter) into a warmed vial and the capped vial was plunged into an ice bath. No immediate precipitation was observed after approximately 20 minutes and the vial was placed in the refrigerator (2-8° C.). After 7 days, the solvent was decanted to recover the solids, and solids were allowed to air dry in the fume hood for 5 days to yield white plates and elongated needles. The white plate and elongated needle solids were determined to be oxymorphone HCl, Form K.

Example 16

Preparation of Form L

Oxymorphone HCl (1.4541 g, Form A) was combined with tert-butanol (50 mL) in a round bottom flask (125 mL) with sonication. Solids remained. Hydrochloric acid (5.144 mL of 0.985N in water) was added. Water (5.0 mL) was added, and after sonication the slightly cloudy solution was filtered (5.0 µm filter) into a clean flask. The solution was frozen in a bath of liquid nitrogen and placed in a lyophilizer jar prior to placing on to a freeze dryer. After 3 days, the flask was removed from the freeze dryer to yield a solid sample exhibiting a mixture of crystalline forms. A portion of this sample (224.4 mg) was placed in a 20 mL glass vial. Ethanol (5 mL) was added to the vial and the sealed vial placed on a shaker block (60° C.). After approximately 17.5 hours most of the solids dissolved. The vial was placed in an ice-water bath and the solution stirred with a magnetic stir bar. After approximately 3 hours the solids were recovered via vacuum filtration while still cold to yield Form L oxymorphone HCl.

Example 17

Preparation of Form M

Oxymorphone HCl, Form A (196.0 mg) was weighed into a 1-dram vial. Ethanol (1 mL) was added plus a magnetic stir bar and the vial capped, sealed with PARAFILM and placed on a shaker block (60° C.) for three days. The solids were recovered using vacuum filtration and subsequently allowed to air-dry to yield Form M oxymorphone HCl.

Example 18

Preparation of Form a Single Crystal

Oxymorphone HCl, Form B (75.1 mg) was dissolved in acetonitrile (5 mL) and water (0.6 mL). Dissolution was achieved with sonication and shaking. The resulting clear solution was filtered through a 0.2 µm filter into a clean vial. The filtered solution was then allowed to evaporate at ambient temperature. Needles and tablets exhibiting birefringence and extinction formed over a period of time and a single crystal of Form A was harvested and submitted for single crystal structure determination.

Example 19

Preparation of Form B Single Crystal

Oxymorphone HCl, Form B (37.9 mg) solids were dissolved in water (200 µL). Dissolution was achieved with sonication and shaking. One hundred microliters of the resulting clear solution was pipetted into a clean vial. The vial was placed in a chamber containing acetone (2 mL) and the chamber was sealed. White plates exhibiting birefringence and extinction formed over a period of time and a single crystal of Form B was harvested and submitted for single crystal structure determination.

Example 20

Preparation of Form H Single Crystal

Oxymorphone HCl, as solids consisting predominantly of Form B (8.0 mg) was combined with acetonitrile/water (20/0.1 v/v, 4 ml). Solids remained after sonication (approximately 45 minutes). The sample was filtered (0.2 µm nylon syringe filter) into a clean vial. The vial was placed uncapped in a larger vial containing acetonitrile (3 ml) and the larger vial capped. Crystals of Form H were submitted in solution for structure determination.

Example 21

Solid, Oral Dosage Form—Prophetic Example

As a specific embodiment of an oral composition, 100 mg of the oxymorphone HCl, Form B is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A form of oxymorphone HCl selected from the group consisting of Form B, Form C, Form D, Form F, Form G, Form H, Form J, Form K, Form L and Form M; wherein:
   Form B has pXRD °2θ peaks at about 7.98, about 9.85, about 10.68, about 11.55 and about 14.70;
   Form C has pXRD °2θ peaks at about 7.83 and about 12.31;
   Form D has pXRD °2θ peaks at about 6.96, about 10.55, about 12.34 and about 15.03;
   Form F has pXRD °2θ peaks at about 9.78, about 10.71, about 11.06 and about 12.03;
   Form G has pXRD °2θ peaks at about 8.12, about 9.88, about 13.27 and about 13.79;
   Form H has pXRD °2θ peaks at about 6.60, about 7.91 and about 11.30;
   Form J has pXRD °2θ peaks at about 5.19, about 5.50, about 6.02 and about 11.07;
   Form K has pXRD °2θ peaks at about 8.08, about 12.48 and about 12.89;
   Form L has pXRD °2θ peaks at about 9.58, about 10.20 and about 12.56; and
   Form M has pXRD °2θ peaks at about 5.70, about 11.44 and about 13.47.

2. A form of oxymorphone HCl selected from the group consisting of Form B, Form C, Form D, Form F, Form G, Form H, Form J, Form K, Form L and Form M; wherein:
   Form B has pXRD °2θ peaks at 7.98, 9.85, 10.68, 11.55, 14.04 and 14.70;
   Form C has pXRD °2θ peaks at 7.83, 10.74, 11.64, 12.31, 14.23 and 15.44;
   Form D has pXRD °2θ peaks at 6.96, 10.55, 11.74, 12.3415.03 and 1538;
   Form F has pXRD °2θ peaks at 9.78, 10.71, 12.03, 12.86, 13.58 and 16.49;
   Form G has pXRD °2θ peaks at 8.12, 9.88, 11.82, 12.34, 13.27 and 13.79;
   Form H has pXRD °2θ peaks at 6.60, 7.91, 8.36, 10.40, 11.30 and 11.96;
   Form J has pXRD °2θ peaks at 5.19, 5.50, 6.02, 7.78, 8.37, 10.38, 11.07, 11.90, 12.07 and 12.76;
   Form K has pXRD °2θ peaks at 8.08, 12.48, 12.89, 15.73, 16.22 and 18.12;
   Form L has pXRD °2θ peaks at 9.58, 9.89, 10.20, 11.24, 12.56 and 15.22; and
   Form M has pXRD °2θ peaks at 5.70, 11.44, 2.92, 13.06, 13.47 and 14.14.

3. A form of oxymorphone HCl selected from the group consisting of Form B, Form C, Form D, Form F, Form G, Form H, Form J, Form K, Form L and Form M; wherein:
   Form B has pXRD °2θ peaks at 7.98, 10.68, 11.55, 14.70, 16.18, 17.19 and 19.12;
   Form C has pXRD °2θ peaks at 7.83, 10.74, 11.64, 12.31, 14.23, 15.44, 16.20, 17.62 and 17.97;
   Form D has pXRD °2θ peaks at 6.96, 10.55, 11.74, 12.34, 15.03, 15.86, 16.07, 17.35, 17.59 and 19.76;
   Form F has pXRD °2θ peaks at 9.78, 10.71, 11.06, 12.03, 16.73 and 19.75;
   Form G has pXRD °2θ peaks at 8.12, 13.27, 13.79, 15.80 and 16.18;
   Form H has pXRD °2θ peaks at 8.36, 11.30, 11.96, 13.20, 15.9, 18.02 and 19.99;
   Form J has pXRD °2θ peaks at 5.19, 5.50, 6.02, 7.78, 8.37, 10.38, 11.07, 11.90, 12.07, 12.76, 15.50 and 16.57;
   Form K has pXRD °2θ peaks at 8.08, 12.48, 12.89, 15.73, 16.22, 18.12, 19.05 and 20.51;

Form L has pXRD °2θ peaks at 9.58, 9.89, 10.20, 11.24, 16.33, 19.10 and 19.23; and Form M has pXRD °2θ peaks at 12.92, 13.06, 13.47, 14.14 and 17.30.

4. A form of oxymorphone HCl as in claim 1, wherein, as measured by Differential Scanning calorimetry (DSC):

Form B is characterized by an endotherm at about 126° C.;

Form D is characterized by an endotherm at about 163° C.;

Form J is characterized by a first endotherm at about 154° C. and a second endotherm at about 164° C.; and Form M is characterized by an endotherm at about 183° C.

5. A form of oxymorphone HCl as in claim 1, which is about 90% to about 100% pure.

6. A form of oxymorphone HCl as in claim 1, which is about 98% to about 100% pure.

7. A pharmaceutical composition comprising a pharmaceutically acceptable carrier and a form of oxymorphone HCl as in claim 1.

8. A pharmaceutical composition made by mixing a form of oxymorphone HCl as in claim 1 and a pharmaceutically acceptable carrier.

9. A process for making a pharmaceutical composition comprising mixing a form of oxymorphone HCl as in claim 1 and a pharmaceutically acceptable carrier.

10. A method of providing an analgesic effect, comprising administering to a subject in need thereof, a therapeutically effective amount of a form of oxymorphone HCl as in claim 1.

11. A form of oxymorphone HCl as in claim 2, which is about 90% to about 100% pure.

12. A form of oxymorphone HCl as in claim 2, which is about 98% to about 100% pure.

13. A pharmaceutical composition comprising a pharmaceutically acceptable carrier and a form of oxymorphone HCl as in claim 2.

14. A pharmaceutical composition made by mixing a form of oxymorphone HCl as in claim 2 and a pharmaceutically acceptable carrier.

15. A process for making a pharmaceutical composition comprising mixing a form of oxymorphone HCl as in claim 2 and a pharmaceutically acceptable carrier.

16. A method of providing an analgesic effect, comprising administering to a subject in need thereof, a therapeutically effective amount of a form of oxymorphone HCl as in claim 2.

17. A form of oxymorphone HCl as in claim 4, which is about 90% to about 100% pure.

18. A form of oxymorphone HCl as in claim 4, which is about 98% to about 100% pure.

19. A pharmaceutical composition comprising a pharmaceutically acceptable carrier and a form of oxymorphone HCl as in claim 4.

20. A pharmaceutical composition made by mixing a form of oxymorphone HCl as in claim 4 and a pharmaceutically acceptable carrier.

21. A process for making a pharmaceutical composition comprising mixing a form of oxymorphone HCl as in claim 4 and a pharmaceutically acceptable carrier.

22. A method of providing an analgesic effect, comprising administering to a subject in need thereof, a therapeutically effective amount of a form of oxymorphone HCl as in claim 4.

* * * * *